(12) United States Patent
Fukui

(10) Patent No.: US 7,881,788 B2
(45) Date of Patent: Feb. 1, 2011

(54) HEART TREATMENT APPARATUS AND HEART TREATMENT METHOD

(75) Inventor: Yoshihito Fukui, Kanagawa (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 817 days.

(21) Appl. No.: 10/569,648

(22) PCT Filed: Aug. 19, 2004

(86) PCT No.: PCT/JP2004/012248

§ 371 (c)(1),
(2), (4) Date: Dec. 4, 2006

(87) PCT Pub. No.: WO2005/018739

PCT Pub. Date: Mar. 3, 2005

(65) Prior Publication Data

US 2007/0118178 A1 May 24, 2007

(30) Foreign Application Priority Data

Aug. 26, 2003 (JP) .............................. 2003-208896

(51) Int. Cl.
*A61N 1/362* (2006.01)
(52) U.S. Cl. ...................................................... 607/14
(58) Field of Classification Search ............... 607/4, 607/5, 14
See application file for complete search history.

(56) References Cited

U.S. PATENT DOCUMENTS

| 5,199,428 A | 4/1993 | Obel et al. |
| 5,356,425 A | 10/1994 | Bardy et al. |
| 5,507,784 A | 4/1996 | Hill et al. |
| 6,134,470 A * | 10/2000 | Hartlaub ....................... 607/14 |
| 6,205,359 B1 * | 3/2001 | Boveja ......................... 607/45 |
| 2002/0107553 A1 | 8/2002 | Hill et al. |
| 2002/0165586 A1 | 11/2002 | Hill et al. |

FOREIGN PATENT DOCUMENTS

| EP | 0 530 354 B1 | 3/1993 |
| EP | 0 647 149 B1 | 4/1995 |
| JP | 7-504596 A | 5/1995 |

(Continued)

OTHER PUBLICATIONS

Supplemental European Search Report dated Apr. 12, 2010.

*Primary Examiner*—George R Evanisko
(74) *Attorney, Agent, or Firm*—Buchanan Ingersoll & Rooney PC

(57) ABSTRACT

Precursor of fatal arrhythmia is detected and by setting the tolerance level for carrying out nerve stimulation depending on the severity degree of the precursor, significant variation of the heart rate is suppressed and induction of the fatal arrhythmia is repressed. For this purpose, precursor of tachyarrhythmia occurrence such as premature contraction, ST change, repolarization abnormality or the like is detected and the lower-limit of the atrium interval which becomes the tolerance level of the nerve stimulation is set according to the detected result. Then, it is constituted according to the precursor of aforesaid tachyarrhythmia such that time for making the nerve stimulation means in an operation state is to be adjusted or nerve stimulation is to be carried out as much as the heart rate of a predetermined number of times.

10 Claims, 18 Drawing Sheets

FOREIGN PATENT DOCUMENTS

| | | |
|---|---|---|
| JP | 2620819 B2 | 6/1997 |
| JP | 2004-533297 A | 11/2004 |
| WO | WO 92/16257 A1 | 10/1992 |
| WO | WO 94/00190 A1 | 1/1994 |
| WO | WO 02/096512 A1 | 12/2002 |

* cited by examiner

HEART TREATMENT APPARATUS AND HEART TREATMENT METHOD

TECHNICAL FIELD

The present invention relates to a heart treatment apparatus for preventing occurrence of tachyarrhythmia by electrical stimulation of vagus nerve and more particularly relates to a heart treatment apparatus and a heart treatment method in which it is possible to control the electrical stimulation of the vagus nerve in response to precursor detection of the tachyarrhythmia occurrence.

BACKGROUND ART

In the past, there was proposed an apparatus having an object for preventing atrial fibrillation from being induced by the increase of the heart rate in which vagus nerve (fat pad) is stimulated if the spontaneous heart rate exceeds a predetermined threshold (see, for example, PCT Jap. laid-open patent publication H7-504596 [lower right column of page 3]). This fat pad exists by accompanying a sino-atrial node or an atrio-ventricular node and the fat pad relating to the sino-atrial node exists at a bended entrance of a right pulmonary vein and is positioned along a ventral atrioventricular groove for most people. Also, the fat pad relating to the atrioventricular node is positioned at a bended coupling portion of a postcaval vein and a subordinate left atrium and is positioned along a dorsal atrioventricular groove for most people.

The apparatus described in the PCT Jap. laid-open patent publication H7-504596 T (lower right column of page 3) is a coupling pacemaker/fat pad stimulator which is to be implanted particularly in a patient who has atrial fibrillation or atrial flutter generating repetitively and who cannot receive sufficient procedure by a medical agent and it is constituted therein in order to sense occurrence of a rapid ventricle rate and to induce absolute or relative heart block such that a stimulation pulse for stimulating the fat pad accompanying the atrioventricular node is to be generated.

Then, the stimulation to the fat pad of the atrioventricular node induces the increase of the heart block, decreases ratio of atrium depolarization transmitted to the ventricle and slows down the ventricle rate. Consequently, the apparatus described in the Patent Reference 1 possesses an operation of a pacemaker which slows down heartbeat rate of the heart by the fat pad stimulation.

However, there is a case in which a serious heart damage occurs by other factors even in a case when the heart rate is not high. Particularly, for a patient who has an organic heart disease such as myocardial infarction, cardiomyopathy or the like, the degenerated, hypertrophied, fibrotic lesioned part and the peripheral part thereof of the myocardium and the endocardium become in an unstable state electrically and this electrical instability causes shortening of a refractory period, forming of an excitation reentry path accompanying thereof and accentuation of automaticity in the heart muscle or in an excitation conducting system or the like so as to make a fatal arrhythmia to occur easily. Consequently, there is a possibility in the apparatus described in the Patent Reference 1 that a fatal arrhythmia which cannot be prevented may occur.

In advance of the occurrence of the fatal arrhythmia, it has been recognized that occurrence of ventricular premature contraction, abnormality of ventricular repolarization process, change of electrogram ST potential or the like is caused and it has been considered such that all of them are important parameters as the precursor of the fatal arrhythmia. The ventricular premature contraction means a ventricular contraction which occurs earlier than timing predicted as a normal rhythm and if this triggers a reentry circuit formed in a heart muscle, ventricular tachycardia or ventricular fibrillation occurs due to reentry. Early afterdepolarization caused when repolarization of action potential of the heart muscle is damaged, delayed afterdepolarization in which depolarization of membrane potential is caused just after the end of repolarization or the like has been recognized for repolarization abnormality and it has been considered such that either one of those of depolarization has an occurrence mechanism of the ventricular tachycardia or the ventricular fibrillation by triggering a new excitation when the amplitude increases and reaches a threshold.

The ST change occurs by myocardial ischemia or myocardial infarction and an oxygen-deprived state of the heart muscle accompanying the myocardial ischemia or the myocardial infarction encourages electrical instability in which the fatal arrhythmia occurs easily. The electrical instability strongly receives influence of a functional factor such as an autonomic nerve or a heart rate and in particular, increase of the oxygen consumption of the heart muscle accompanying the heart rate increase or accentuation of the sympathetic nerve tension increases electrical instability which is primarily owned by a patient of an organic heart disease such as myocardial infarction, cardiomyopathy or the like and it makes a state for inducing a fatal arrhythmia easily by premature contraction, repolarization abnormality or ST change.

DISCLOSURE OF THE INVENTION

In view of aforesaid problems, the present invention has an object in which the heart rate is lowered and oxygen consumption of the heart muscle is reduced by controlling the vagus nerve stimulation in response to detection precursor of fatal arrhythmia such that the heart rate falls into a predetermined tolerance level and at the same time, correction of repolarization non-uniformity is attempted by suppressing heart rate variation and further, inducing of fatal arrhythmia is repressed by repressing the sympathetic nerve tension antagonistically owing to the vagus nerve stimulation.

In order to achieve the object of the present invention, the heart treatment apparatus of the present invention has a feature in which there are provided with nerve stimulation means for generating a nerve stimulation signal which stimulates a vagus nerve, tachyarrhythmia precursor detection means for detecting a precursor of a tachyarrhythmia occurrence, heart activity measuring means for measuring a heart activity, means for defining a tolerance level of the heart activity, and control means for connecting these of the nerve stimulation means and the tachyarrhythmia precursor detection means to the heart activity measuring means; and the control means responds to the tachyarrhythmia precursor detection means and the nerve stimulation means is controlled such that the output of the heart activity measuring means is to be maintained within the tolerance level.

Also, the heart treatment method of the present invention has a feature in which there are provided a nerve stimulation step for generating a nerve stimulation signal which stimulates a vagus nerve, a step for detecting a precursor of a tachyarrhythmia occurrence, a step for measuring a heart activity, and a step for defining a tolerance level of the heart activity; and the nerve stimulation is controlled such that the measured output of the heart activity is to be maintained within the tolerance level in response to the precursor detection of aforesaid tachyarrhythmia occurrence.

In a preferable mode of the heart treatment apparatus and the heart treatment method according to the present invention, it has a feature in which the precursor detection of the tachyarrhythmia occurrence is performed according to electrogram and this precursor is any one of premature contraction, ST change and repolarization abnormality.

Also, in a preferable mode of the present invention, it is constituted such that the nerve stimulation control carried out in response to the tachyarrhythmia precursor detection is to be performed in a predetermined period which is adjusted according to the output of the tachyarrhythmia precursor detection.

Further, in a preferable mode of the present invention, it has a feature in which the control of the nerve stimulation which is performed in response to the tachyarrhythmia precursor detection is carried out for a period until the heart activity reaches a predetermined number of times which is adjusted according to the output of the tachyarrhythmia precursor detection.

Then, when the measured output of the heart activity is out of the tolerance level, a nerve stimulation signal is to be generated wherein it has a feature that the nerve stimulation signal parameter which the nerve stimulation means generates is adjusted according to difference between the output of the heart activity measuring and the tolerance level of aforesaid heart activity.

Then, the nerve stimulation signal parameter is at least one of period between pulses, pulse width, number of pulses, pulse current, pulse voltage, delay time, rest time and repetition times or a combination of a plurality of ones selected from these.

Further, in a preferable mode of the present invention, it has a feature that aforesaid heart activity is the heartbeat and the heartbeat measurement by the heart activity measuring is measurement of heartbeat interval or heart rate, and it has a feature that aforesaid tolerance level is defined to a heartbeat interval range longer than a predetermined lower-limit of a heartbeat interval or to a heart rate range lower than said predetermined upper-limit of a heart rate and the lower-limit of the heartbeat interval or the upper-limit of the heart rate is adjusted according to the output of the tachyarrhythmia precursor detection.

Then, the adjustment of the lower-limit of the heartbeat interval or the upper-limit of the heart rate is one for making it to be longer than a heartbeat interval at a normal time or to be lower than the heart rate at a normal time by a predetermined amount wherein it is also possible to make aforesaid predetermined amount to be a fixed value and it is also possible to make it to be a predetermined ratio of the heartbeat interval or the heart rate at a normal time.

According to the heart treatment apparatus and the heart treatment method of the present invention, tolerance level of heart activity is set in response to precursor detection of tachyarrhythmia occurrence and it is possible to carry out nerve stimulation such that the heart activity is maintained within the tolerance level, so that it is possible to optimize electrical instability of the ventricle after the precursor for a patient of an organic heart disease such as myocardial infarction or cardiomyopathy and to suppress occurrence of fatal arrhythmia.

Also, tolerance level of the heart activity and stimulation time of the vagus nerve is controlled by comprehensively observing kinds of detected precursors and results of measured heart activities, so that treatment by the vagus nerve stimulation is never carried out excessively and consequently, it is possible to suppress limitation of a patient's exercise capability to be small.

BEST MODE FOR CARRYING OUT THE INVENTION

Figure 1:
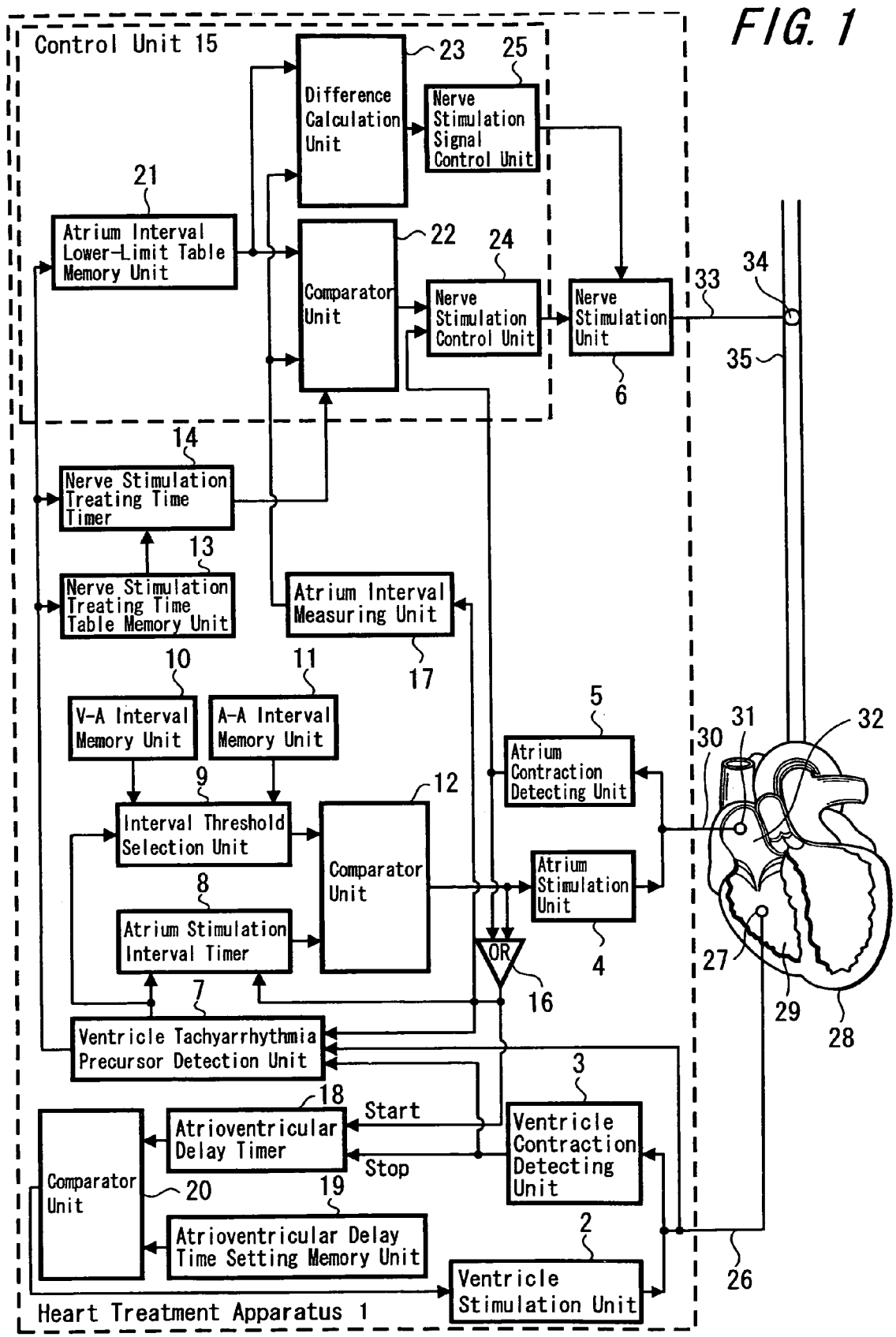
FIG. 1 is a block diagram showing a first exemplified embodiment according to a heart treatment apparatus of the present invention.

Hereinafter, a first exemplified embodiment of the heart treatment apparatus by the present invention will be explained according to a block diagram of FIG. 1.

A heart treatment apparatus 1 of the present invention is constituted by a ventricle stimulation unit 2 for generating a ventricle stimulation pulse stimulating a right ventricle 29 of a heart 28, a ventricle contraction detecting unit 3 for detecting a contraction of a right ventricle 29, an atrium stimulation unit 4 for generating an atrium stimulation pulse stimulating a right atrium 32 of the heart 28, an atrium contraction detecting unit 5 for detecting a contraction of a right atrium 32, a nerve stimulation unit 6 for generating a nerve stimulation signal stimulating a vagus nerve 35, a ventricle tachyarrhythmia precursor detection unit 7 for detecting precursor of ventricle tachyarrhythmia such as ventricular premature contraction or the like according to information of ventricle contraction detection, electrogram information from a ventricle detection electrode 27 or atrium stimulation and atrium contraction detection (Hereinafter, named as "atrium event". Similarly, ventricle stimulation and ventricle contraction detection are named as "ventricle event".), an atrium stimulation interval timer 8 for starting clocking by an output of the ventricle tachyarrhythmia precursor detection unit 7 when precursor of ventricular premature contraction or the like was detected or by detection of an atrium event, an interval threshold selection unit 9 for changing over threshold of the atrium stimulation interval timer 8 also by the output of the ventricle tachyarrhythmia precursor detection unit 7 when the precursor of ventricular premature contraction or the like was detected, a V-A interval memory unit 10 for storing a time period from a ventricular premature contraction detection until the atrium stimulation selected when the ventricular premature contraction was detected, an A-A interval memory unit 11 for storing a time period from an atrium event detection until a next atrium stimulation selected when the ventricular premature contraction is not detected, a comparator unit 12 for comparing clocking time of the atrium stimulation interval timer 8 and the V-A interval or the A-A interval selected by the interval threshold selection unit 9, a nerve stimulation treating time table memory unit 13 for selecting nerve stimulation treating time in response to the precursor detected by the ventricle tachyarrhythmia precursor detection unit 7, a nerve stimulation treating time timer 14 for operating as a down-counter which is loaded with the output of the nerve stimulation treating time selected by the nerve stimulation treating time table memory unit 13, a control unit 15 for carrying out a control operation for a nerve stimulation according to the content of the precursor detected by the ventricle tachyarrhythmia precursor detection unit 7, an OR circuit 16 for emanating an output when an atrium event (atrium contraction detection, atrium stimulation or the like) is detected, an atrium interval measuring unit 17 for measuring an interval of the atrium event from the output of the OR circuit 16, an atrioventricular delay timer 18 for starting clocking by an output of the OR circuit 16 and for stopping clocking by an output of the ventricle contraction detecting unit 3, an atrioventricular delay time setting memory unit 19 for storing atrioventricular delay time which becomes a reference, and a comparator unit 20 for emanating an output when the clocking time of the atrioventricular delay timer 18 exceeds the set value stored in the atrioventricular delay time setting memory unit 19.

Also, the control unit 15 is constituted by an atrium interval lower-limit table memory unit 21 which is supplied with a precusor signal from the ventricle tachyarrhythmia precusor detection unit 7 and selects a lower-limit of an atrium interval carrying out a stimulation of the vagus nerve 35 in response to this precursor signal, a comparator unit 22 which is made to be in an operation state by an output of the nerve stimulation treating time timer 14 and compares an atrium interval measured by the atrium interval measuring unit 17 and a lower-limit of an atrium interval selected in the atrium interval lower-limit table memory unit 21, a difference calculation unit 23 for calculating the difference of the aforesaid measured atrium interval and the selected lower-limit of the atrium interval, a nerve stimulation control unit 24 for receiving outputs of the comparator unit 22 and the atrium contraction detecting unit 5 and for generating an output with respect to the nerve stimulation unit 6 at a timing of the atrium contraction detection, and a nerve stimulation signal control unit 25 for selecting a nerve stimulation parameter for adjusting stimulation degree of the nerve stimulation signal in response to the calculated difference from the difference calculation unit 23.

In the heart treatment apparatus 1 constituted as described above, the ventricle stimulation unit 2 and the ventricle contraction detecting unit 3 are connected to the ventricle stimulation/detection electrode 27 by means of a common ventricle electrode lead 26. Then, similarly, also the atrium stimulation unit 4 and the atrium contraction detecting unit 5 are connected to an atrium stimulation/detection electrode 31 through a common atrium electrode lead 30. The ventricle stimulation/detection electrode 27 and the atrium stimulation/detection electrode 31 are arranged in the right ventricle 29 and the right atrium 32 of the heart 28 respectively.

Figure 2:
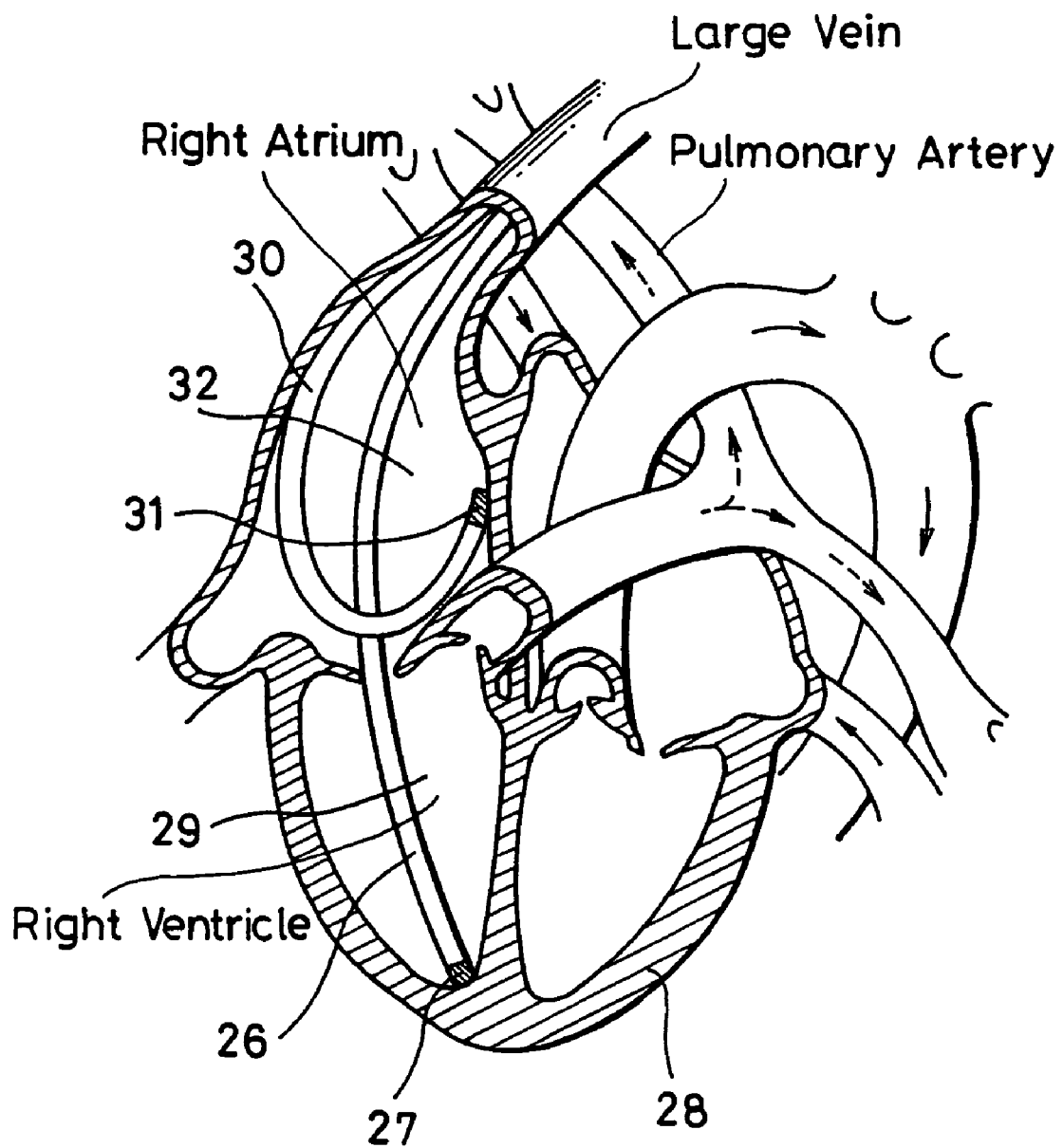
FIG. 2 is an arrangement diagram of ventricle and atrium electrode leads and respective stimulation electrodes to a heart, which are used in the heart treatment apparatus of the present invention.

As the electrode for the heart, there are a myocardial electrode implanted in a heart muscle which is a so-called myocardium and a catheter electrode whose electrode is inserted until the heart by way of the large vein and according to the present invention, a catheter electrode is used as shown in FIG. 2. Both one of the ventricle electrode lead 26 and the atrium electrode lead 30 are initially introduced from the large vein to the right atrium 32 of the heart 28. The atrium electrode lead 30 inserted from the large vein to the right atrium 32 is inserted such that the tip portion thereof bended in J-shape is to be hooked on the pouched right auricle projecting from the right atrium wall and arranged such that the atrium stimulation/detection electrode 31 is to be contacted to the inner wall of right auricle. Also, similarly, the ventricle electrode lead 26 inserted into the right atrium 32 from the large vein enters into the right ventricle 29 passing through an auriculoventricular valve and is arranged such that the ventricle stimulation/detection electrode 27 located at the tip portion of the ventricle electrode lead 26 is to be contacted to the lowermost portion of the right ventricle 29.

Also, although it is not shown in FIG. 2, the nerve stimulation unit 6 is connected to a nerve stimulation electrode 34 through a nerve electrode lead 33 and the nerve stimulation electrode 34 is fixed by being wound around the vagus nerve 35. As the region on which the nerve stimulation electrode 34 is wound around, a neck portion region or a right central position of an external carotid artery is preferable. Also, it is also possible to arrange the nerve stimulation electrode 34 such that the vagus nerve 35 adjacent to a blood vessel wall is to be stimulated by placing the catheter electrode in the blood vessel. In that case, inside of a subclavian vein is preferable for the arrangement region thereof.

Next, the operation of a first exemplified embodiment of the heart treatment apparatus according to the present invention shown in FIG. 1 will be explained.

With respect to the ventricle tachyarrhythmia precursor detection unit 7, various data necessary for judging the precursor content such as electrogram information from the ventricle detection electrode 27 are supplied. Also, other than the above, a detection signal of ventricle contraction from the ventricle contraction detecting unit 3 and atrium event information from the OR circuit 16 are supplied thereto. As the precursor detected by the ventricle tachyarrhythmia precursor detection unit 7, there are various precursors in connection with abnormality degree of the tachyarrhythmia as shown in table 1. For example, as representative one of the precursor, there is ventricular premature contraction (PVC) in which excitation is caused by a ventricle region having a rhythm different from normal earlier than an expected moment. It is possible to detect the premature contraction using the ventricle contraction detected signal and the atrium event information by not being accompanied with an atrium event before the detection of the ventricle contraction. Also, the electrogram waveform of the premature contraction is generally accompanied with a large QRS wave having wide width, so that it is possible to detect it from the electrogram information.

TABLE 1

| precursor number (N) | precursor | nerve stimulation treating time | lower limit of atrium interval |
|---|---|---|---|
| 0 | none | — | — |
| 1 | single PVC | T1 | AAI1 |
| 2 | two successive PVC's <Couplet> | T2 | AAI1 |
| 3 | three or more successive PVC's <Short-run> repolarization abnormality | T3 | AAI1 |
| 4 | PVC <R on T> ST Increase ST Decrease | T4 | AAI1 |

(Example of Nerve Stimulation Treating Time Control: T1 < T2 < T3 < T4)

Relation Between Ventricle Tachyarrhythmia Precursor and Nerve Stimulation Treating Time or Lower-Limit of Atrium Interval Table 1 is a table in which precursors are classified depending on risks of tachyarrhythmia occurrence and are made to be correspondent with the precursor number N wherein it is shown that the larger the precursor number is, the higher the risk of the tachyarrhythmia occurrence is. It is classified in table 1 such that the precursor number is made to be 0 in case of no precursor, the precursor number is made to be 1 in a case when single premature contraction is caused, the precursor number is made to be 2 in a case when it is caused twice continuously (two successive PVC's: Couplet) and the precursor number is made to be 3 in a case when the premature contraction is caused three times or more continuously (three or more successive PVC's: Short-run) and in a case when it is repolarization abnormality (early afterdepolarization, delayed afterdepolarization or the like). Then, there are classified in maximum precursor number 4 PVC (R on T) in which premature contraction appears in the vicinity of a tip-top of a precedent T wave and ST change (increase or lowering) in which ischemia of a ventricle muscle or a state of infarction is to be detected from the content of the electrogram. It should be noted that kinds of precursors to be detected, number of steps of the precursor numbers and correspondence making between the precursor and the precursor number is to be set by a medical doctor according to a clinical state or a clinical history of a patient and alternatively according to a result of an electrophysiologic test or the like.

It is because, in general, it sometimes happens that the premature contraction may trigger a ventricular tachycardia or a ventricular fibrillation for a patient of myocardial infarction or heart failure and if the precursor number is changed and given in response to the continuous degree as described above, the more the number of successive beats is the higher the risk becomes. Also, the vicinity of the tip-top of the T wave on the electrogram is referred to as a vulnerable period and if the premature contraction wave overlaps this period, it is easily shifted to the ventricular fibrillation, so that it is possible to consider that the precursor of R on T type has a particularly high risk for a fatal arrhythmia occurrence.

Also, as for others, there is a high risk for a wave having a short interval between R wave of the premature contraction and R wave just before (coupling interval) or if there is instability such that the coupling interval changes every time of the expression thereof and a wave whose electrogram shape changes every time of the premature contraction occurrence has a high risk. Consequently, it is also possible to consider about these factors for the precursor detection.

Further, ST increase or ST lowering on an electrogram which indicates ischemia of a ventricle muscle or a state of infarction heightens possibility of a fatal arrhythmia occurrence if it changes rapidly. Also, it has been considered that repolarization abnormality such as early afterdepolarization which is caused when repolarization of action potential of the heart muscle is damaged, delayed afterdepolarization in which depolarization of membrane potential is caused just after an end of repolarization or the like is to be an occurrence mechanism of ventricular tachycardia or ventricular fibrillation by triggering a new excitation when the amplitude of any one thereof increases and reaches a threshold. Also, as for others, it is also possible to consider about non-uniformity (QT dispersion) of the electrogram QT interval, T wave variation (T wave Alternans) or delayed potential after QRS (Late potential) with respect to the repolarization abnormality for the precursor detection.

When a ventricle tachyarrhythmia precursor is detected in the ventricle tachyarrhythmia precursor detection unit 7, the ventricle tachyarrhythmia precursor detection unit 7 supplies a signal corresponding to the precursor number N to the nerve stimulation treating time table memory unit 13, the nerve stimulation treating time timer 14 and the atrium interval lower-limit table memory unit 21 of the control unit 15.

The nerve stimulation treating time table memory unit 13 receives the precursor detection signal, selects a nerve stimulation treating time corresponding to the precursor number N among the nerve stimulation treating times T1 to T4 shown in table 1 and loads the time on the nerve stimulation treating time timer 14.

The nerve stimulation treating time timer 14 emanates an output to the comparator unit 22 according to loading of the selected time and activates the comparator unit 22. Then, the nerve stimulation treating time timer 14 operates as a down-counter and makes the comparator unit 22 to be in a non-operating state when counted content becomes "0". Consequently, it happens that the comparator unit 22 is to be activated during a period of the nerve stimulation treating time corresponding to the selected precursor number N.

Setting of the values of the nerve stimulation treating times T1 to T4 is carried out by a medical doctor according to a clinical state or a clinical history of a patient and alternatively according to a result of an electrophysiologic test or the like, wherein usually, it is set such that the larger the precursor number N becomes, that is, the higher the risk of the tachyarrhythmia occurrence becomes, the longer it becomes.

Also, when the atrium interval lower-limit table memory unit 21 receives the precursor detection signal from the ventricle tachyarrhythmia precursor detection unit 7, it selects a lower-limit of an atrium interval according to the precursor number N and supplies this to the comparator unit 22 and the difference calculation unit 23. Here, the selected lower-limit of the atrium interval is an interval defining a lower limit in a permissible atrium interval range. It should be noted that it is needless to say that the lower-limit of the atrium interval corresponds to the upper-limit of the heart rate and if the upper-limit of the heart rate (times/minute) is made to be HRMAX and the lower-limit of the atrium interval (seconds) is made to be AAI, the upper-limit of the heart rate can be derived according to the following equation (1).

$$HRMAX=60/AAI \qquad (1)$$

The comparator unit 22 is supplied with an output of the atrium interval measuring unit 17 and when the comparator unit 22 is in an activating state and when the atrium interval measured by the atrium interval measuring unit 17 is shorter than the lower-limit of the atrium interval selected in the atrium interval lower-limit table memory unit 21, in other words, when the measured heart rate is higher than the upper-limit of the heart rate by saying with respect to the heart rate, an output is emanated from the comparator unit 22 to the nerve stimulation control unit 24. On the other hand, when the comparator unit 22 is in a non-operating state, any output is not emanated to the nerve stimulation control unit 24.

The nerve stimulation control unit 24 is supplied also with an output of the atrium contraction detecting unit 5, the nerve stimulation control unit 24 emanates an output to the nerve stimulation unit 6 at a timing of the atrium contraction detection and the vagus nerve 35 is stimulated by the nerve stimulation electrode 34. The stimulation of the vagus nerve 35 represses the heart activity so as to elongate the atrium interval, so that when the measured atrium interval becomes shorter than the lower-limit of the atrium interval, the atrium interval is controlled by the stimulation of the vagus nerve 35 such that it comes to be in a tolerance level equal to the lower-limit of the atrium interval or more.

In table 1, the lower-limit of the atrium interval is set to a constant value AAI1 without being related to the precursor number N, but as shown in table 2, it is also possible to select it among the lower-limits of the atrium interval AAI1 to AAI4 depending on the precursor number N by making the nerve stimulation treating time selected in the nerve stimulation treating time table memory unit 13 to be a constant value (T1).

TABLE 2

| precursor number (N) | precursor | nerve stimulation treating time | lower limit of atrium interval |
|---|---|---|---|
| 0 | none | — | — |
| 1 | single PVC | T1 | AAI1 |
| 2 | two successive PVC's <Couplet> | T1 | AAI2 |
| 3 | three or more successive PVC's <Short-run> repolarization abnormality | T1 | AAI3 |
| 4 | PVC <R on T> ST Increase ST Decrease | T1 | AAI4 |

(Example of Lower-limit of Atrium Interval Control: AAI1 < AAI2 < AAI3 < AAI4)

Relation Between Ventricle Tachyarrhythmia Precursor and Nerve Stimulation Treating Time or Lower-Limit of Atrium Interval The values of AAI1 to AAI4 in table 2 are to be set similarly as the nerve stimulation treating times by a medical doctor according to a clinical state or a clinical history of a patient and alternatively according to a result of an electrophysiologic test or the like. The lower-limit of the atrium interval is usually set such that the larger the precursor number N becomes, that is, the higher the risk of the tachyarrhythmia occurrence becomes, the longer it becomes.

In the difference calculation unit 23, difference between the atrium interval measured by the atrium interval measuring unit 17 and the lower-limit of the atrium interval selected in the atrium interval lower-limit table memory unit 21 is calculated. Then, the calculated difference is supplied to the nerve stimulation signal control unit 25 and here, a nerve stimulation signal parameter according to the difference is selected among the nerve stimulation parameters stored in the nerve stimulation signal control unit 25 and it is supplied to the nerve stimulation unit 6. The stimulation degree of the vagus nerve 35 by the nerve stimulation unit 6 is adjusted according to this nerve stimulation signal parameter.

It should be noted in this first exemplified embodiment that the nerve stimulation signal parameter is selected by comparing the lower-limit of the atrium interval selected in the atrium interval lower-limit table memory unit 21 and the atrium interval measured by the atrium interval measuring unit 17 according to the comparator unit 22 and the difference calculation unit 23 and the stimulation control of the vagus nerve 35 is carried out, but it is also possible to convert these atrium intervals to heart rates once so as to calculate the heart rate difference and to adjust the nerve stimulation signal parameter which is to be generated in the nerve stimulation unit 6 according to this heart rate difference owing to the relation between the heart rate difference stored in the nerve stimulation signal control unit 25 beforehand and the nerve stimulation signal parameter.

Figure 19:
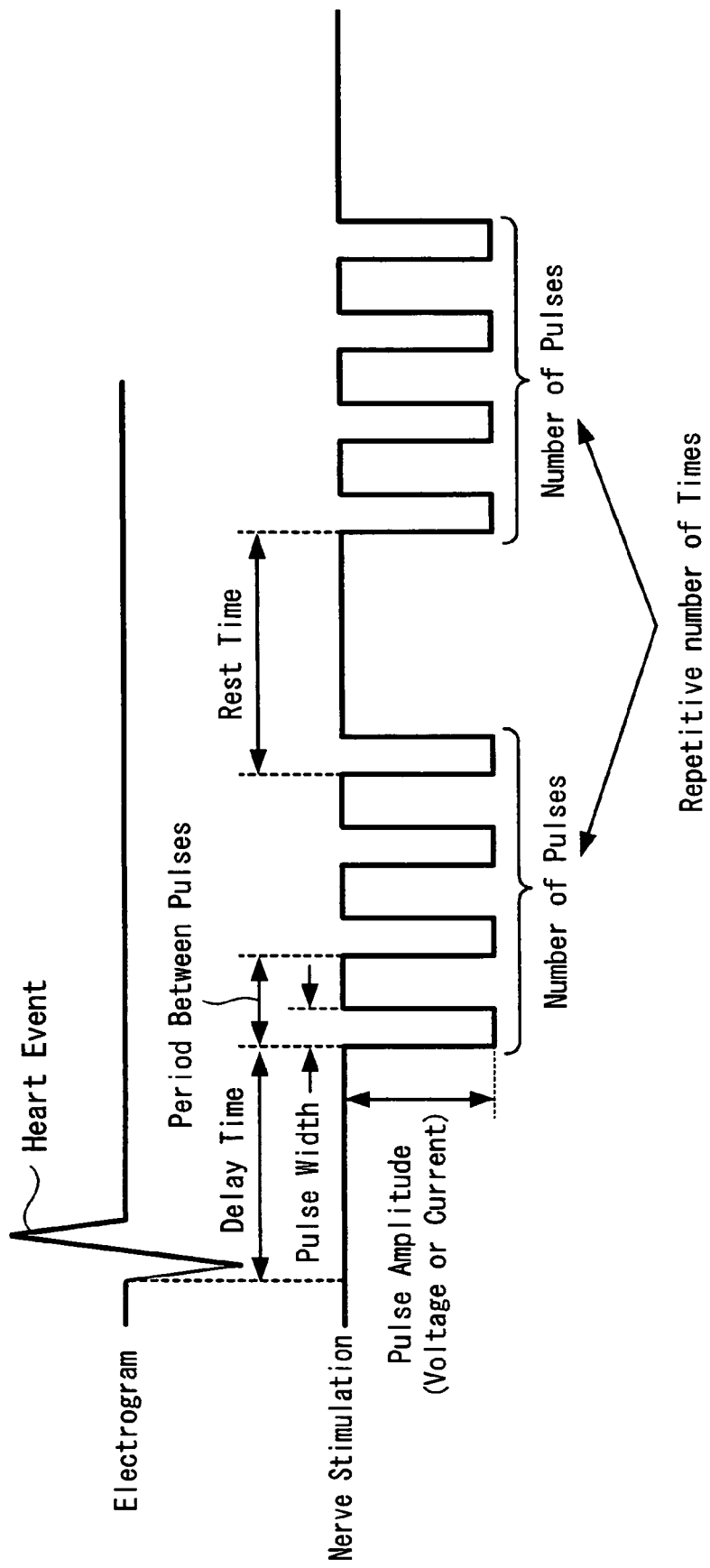
FIG. 19 is a waveform diagram showing parameters of a nerve stimulation signal.

Here, as nerve stimulation signal parameter, period between pulses of the nerve stimulation pulse, pulse width, number of pulses, pulse current, pulse voltage, delay time, rest time, repetition times or the like can be considered. For the control of the nerve stimulation signal parameter, it is possible to carry out the adjustment by selecting one among these parameters, but it is also possible to carry out the control by adjusting a combination of a plurality of ones selected from these. It should be noted that a waveform diagram indicating a relation between these nerve stimulation signal parameters and the electrogram is shown in FIG. 19.

Also, when the premature contraction (PVC) is detected by the ventricle tachyarrhythmia precursor detection unit 7, the detected signal is supplied to the atrium stimulation interval timer 8 and the interval threshold selection unit 9. The atrium stimulation interval timer 8 is reset by the detection of the premature contraction and starts clocking. Also, the interval threshold selection unit 9 selects the V-A interval memory unit 10 when it receives the detection signal of the premature contraction from the ventricle tachyarrhythmia precursor detection unit 7. When the premature contraction is not detected, the A-A interval memory unit 11 is selected. The A-A interval has a value which is obtained by adding the set value stored in the atrioventricular delay time setting memory unit 19 to the V-A interval.

The comparator unit 12 generates an output to the atrium stimulation unit 4 when the clocking time of the atrium stimulation interval timer 8 reaches the V-A interval selected by the interval threshold selection unit 9 and the right atrium 32 is stimulated by the atrium stimulation unit 4 through the atrium stimulation electrode 31. At that time, the interval threshold selection unit 9 is changed over to the selection of the A-A interval memory unit 11. Here, the V-A interval is shorter as compared with the A-A interval by a value of the atrioventricular delay time set value, so that the ventricle event interval after the premature contraction detection becomes V-A interval+atrioventricular delay time set value and becomes equal to the atrium event interval defined by the A-A interval.

The output of the OR circuit 16 to which an output of the atrium contraction detection according to the atrium contraction detecting unit 5 and an output of the comparator unit 12 are added is supplied to the atrioventricular delay timer 18 and makes it to start. The atrioventricular delay timer 18 stops its clocking when there was an output of the ventricle contraction detecting unit 3, but if the clocking time during that period exceeds the set value stored in the atrioventricular delay time setting memory unit 19, in other words, if the atrioventricular delay timer 18 is timeout, an output is emanated from the comparator unit 20 and is transmitted to the ventricle stimulation unit 2. Then, the ventricle stimulation unit 2 stimulates the right ventricle 29 of the heart 28 through the ventricle electrode lead 26 and the ventricle stimulation electrode 27.

Next, the operation of the first exemplified embodiment of the heart treatment apparatus of the present invention will be explained further in detail according to flow diagrams of FIG. 3 to FIG. 6.

Here, the ventricle tachyarrhythmia precursor detection unit 7 can keep a maximum value MN of the precursor number N. MN is a maximum precursor number in which the value of the precursor number N is stored according to the precursor detection and the content thereof is reset when the nerve stimulation treatment which is made to be correspondent with the precursor is finished. Before the content of MN is reset, more specifically, if a new precursor is detected during a period when the nerve stimulation treatment continues, the precursor number of the newly detected precursor and the presently stored precursor number are compared. Then, in a case when the new precursor number is bigger than or equal to the presently stored precursor number, the content of MN is renewed by the new precursor number and at the same time, a nerve stimulation treatment which is made to be correspondent with the new precursor number is started. On the other hand, in a case when the new precursor number is smaller than the presently stored precursor number, the nerve stimulation treatment which is carried out presently continues. In this manner, a nerve stimulation treatment following a precursor whose risk of the tachyarrhythmia occurrence is high becomes possible.

First, as for an operation of an initial state, the maximum value MN of the precursor number N is reset to "0" in the ventricle tachyarrhythmia precursor detection unit 7 (step S1). Next, the timer value of the nerve stimulation treating time timer 14 is set to "0" (step S2) and at the same time, the A-A interval stored in the A-A interval memory unit 11 is selected by the interval threshold selection unit 9 as the threshold of the atrium stimulation interval timer 8 (step S3). Then, the atrium stimulation interval timer 8 is reset (step S4).

Next, it is judged whether or not the atrium stimulation interval timer 8 is timeout (step S5). In a case when the atrium stimulation interval timer 8 is timeout, the comparator unit 12 emanates an output and atrium stimulation is carried out by the atrium stimulation unit 4 (step S6), when the atrium stimulation interval timer 8 is not timeout, it is judged subsequently whether or not premature contraction was detected in the ventricle tachyarrhythmia precursor detection unit 7 (step S7).

Figure 4:
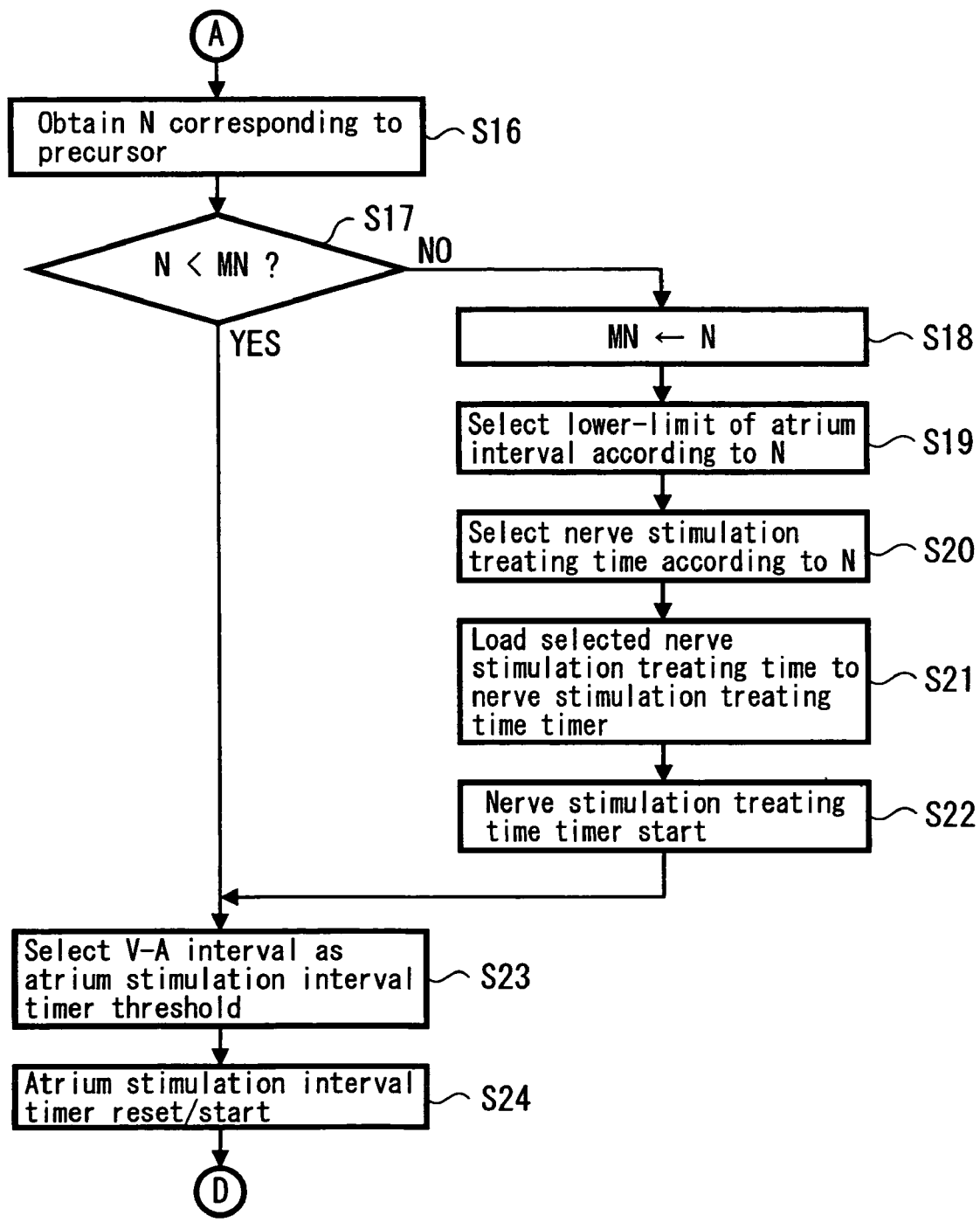
FIG. 4 is a portion of a flow diagram for explaining operation of the first exemplified embodiment according to the heart treatment apparatus of the present invention.

In a case when the premature contraction is detected in judgment step S7, the flow proceeds to (A) of FIG. 4 and when the premature contraction is not detected, it is judged subsequently whether or not atrium contraction was detected in the atrium contraction detecting unit 5 (step S8). In a case when the atrium contraction is detected, the flow proceeds to (B) of FIG. 5 and in a case when the atrium contraction is not detected, the flow returns to judgment step S5 and it is judged whether or not the atrium stimulation interval timer 8 was timeout.

After the atrium stimulation was carried out in step S6, the A-A interval stored in the A-A interval memory unit 11 is again selected as the threshold of the atrium stimulation interval timer 8 (step S9) and the atrium stimulation interval timer 8 is reset (step S10). Further, the clocking of the atrioventricular delay timer 18 is started (step S11).

Next, it is judged whether or not ventricle contraction was detected in the ventricle contraction detecting unit 3 (step S12). If the ventricle contraction is detected, the clocking of the atrioventricular delay timer 18 is stopped (step S13) and in a case when the ventricle contraction is not detected, it is judged whether or not the atrioventricular delay timer 18 is timeout, more specifically, whether or not the atrioventricular delay timer 18 made clocking beyond the set value stored in the atrioventricular delay time setting memory unit 19 (step S14). In a case when the atrioventricular delay timer 18 is not timeout, the flow returns to judgment step S12 and waits for ventricle contraction detection. When the atrioventricular delay timer 18 is timeout, the comparator unit 20 emanates an output to the ventricle stimulation unit 2 and stimulation of the right ventricle 29 of the heart 28 is carried out by the ventricle stimulation electrode 27 (step S15). Subsequently, the flow returns to judgment step S5 and it is judged whether or not the atrium stimulation interval timer 8 was timeout.

Next, operations after the premature contraction is detected in judgment step S7 (after (A) of FIG. 3) will be explained according to a flow diagram of FIG. 4. When the premature contraction is detected in judgment step S7, the flow proceeds to (A) of FIG. 4 and the precursor number N corresponding to the precursor is obtained in the ventricle tachyarrhythmia precursor detection unit 7 (step S16). For example, in a case when the single premature contraction is caused, N=1 is made as shown in table 1 and this is registered as a precursor number in the ventricle tachyarrhythmia precursor detection unit 7.

Figure 6:
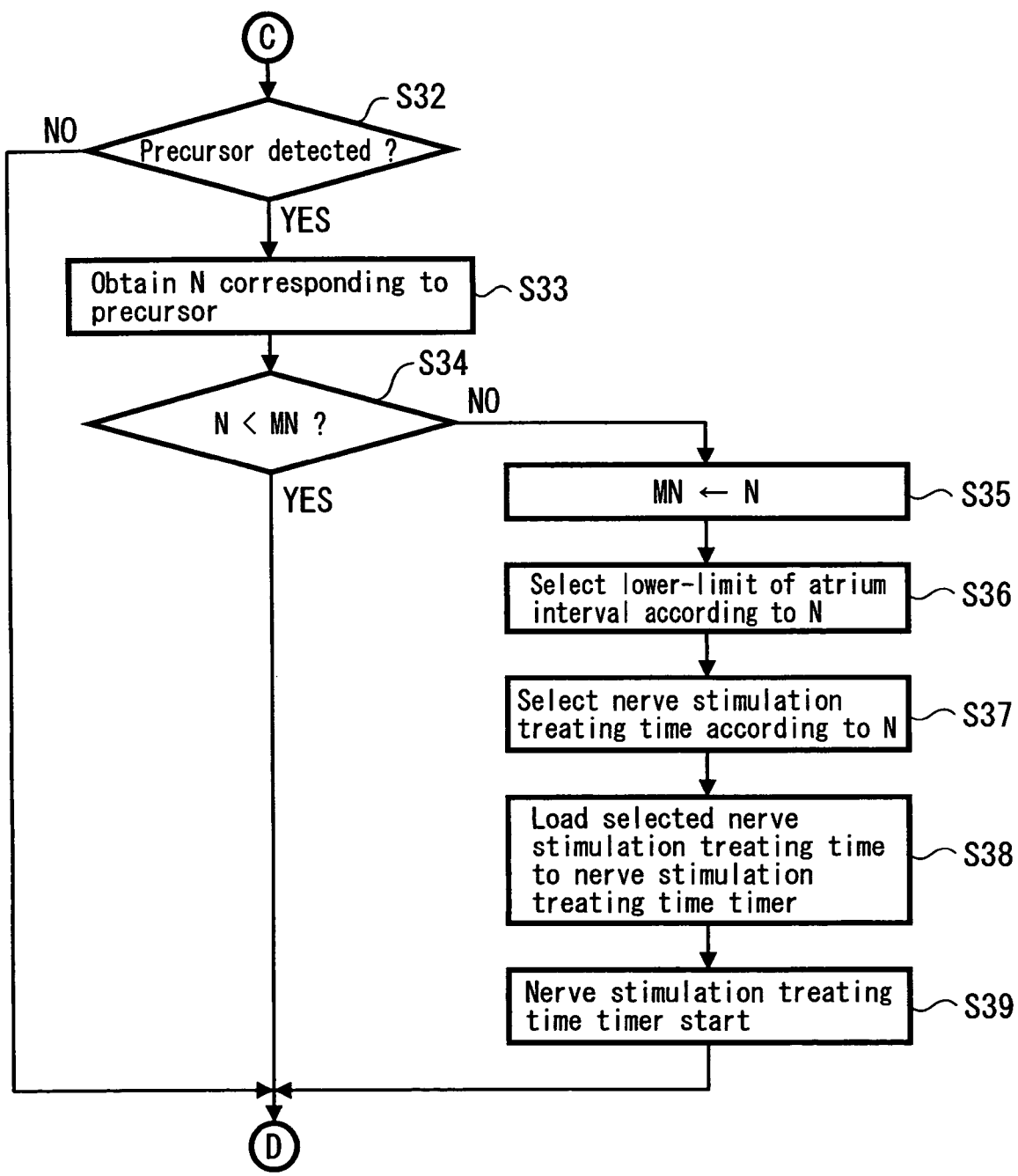
FIG. 6 is a portion of a flow diagram for explaining operation of the first exemplified embodiment according to the heart treatment apparatus of the present invention.

Next, the obtained precursor number N is compared with the maximum precursor number MN (step S17). In step S1 of FIG. 3, the maximum precursor number MN is set to "0", but (D) of FIG. 4 and FIG. 6 is supplied to the preceding stage of judgment step S5 in the flow diagram of FIG. 3, so that there is a case in which MN is not smaller than N (case of equal to or larger).

When N is not smaller than MN in judgment step S17, that is, when MN≦N is true, the value of MN is replaced by the value of N (step S18). Subsequently, the lower-limit of the atrium interval stored in the atrium interval lower-limit table memory unit 21 is selected according to the detected precursor number N (step S19) and further, the nerve stimulation treating time stored in the nerve stimulation treating time table memory unit 13 is selected according to the precursor number N (step S20).

Subsequently, aforesaid selected nerve stimulation treating time is loaded to the nerve stimulation treating time timer 14 (step S21) and the nerve stimulation treating time timer 14 starts clocking (step S22). This clocking continues for a period of the loaded nerve stimulation treating time and stops when aforesaid loaded treating time elapses. During that period, the nerve stimulation treating time timer 14 makes the comparator unit 22 to be activated, that is, to be in an operation state.

When the precursor number N is smaller than the maximum precursor number MN in judgment step S17 and after the nerve stimulation treating time timer 14 starts clocking in step S22, the interval threshold selection unit 9 selects the V-A interval stored in the V-A interval memory unit 10 as the threshold of the atrium stimulation interval timer 8 (step S23). Then at the same time, the atrium stimulation interval timer 8 is reset and the clocking is started (step S24). Subsequently, the flow returns to (D) of FIG. 3.

Figure 5:
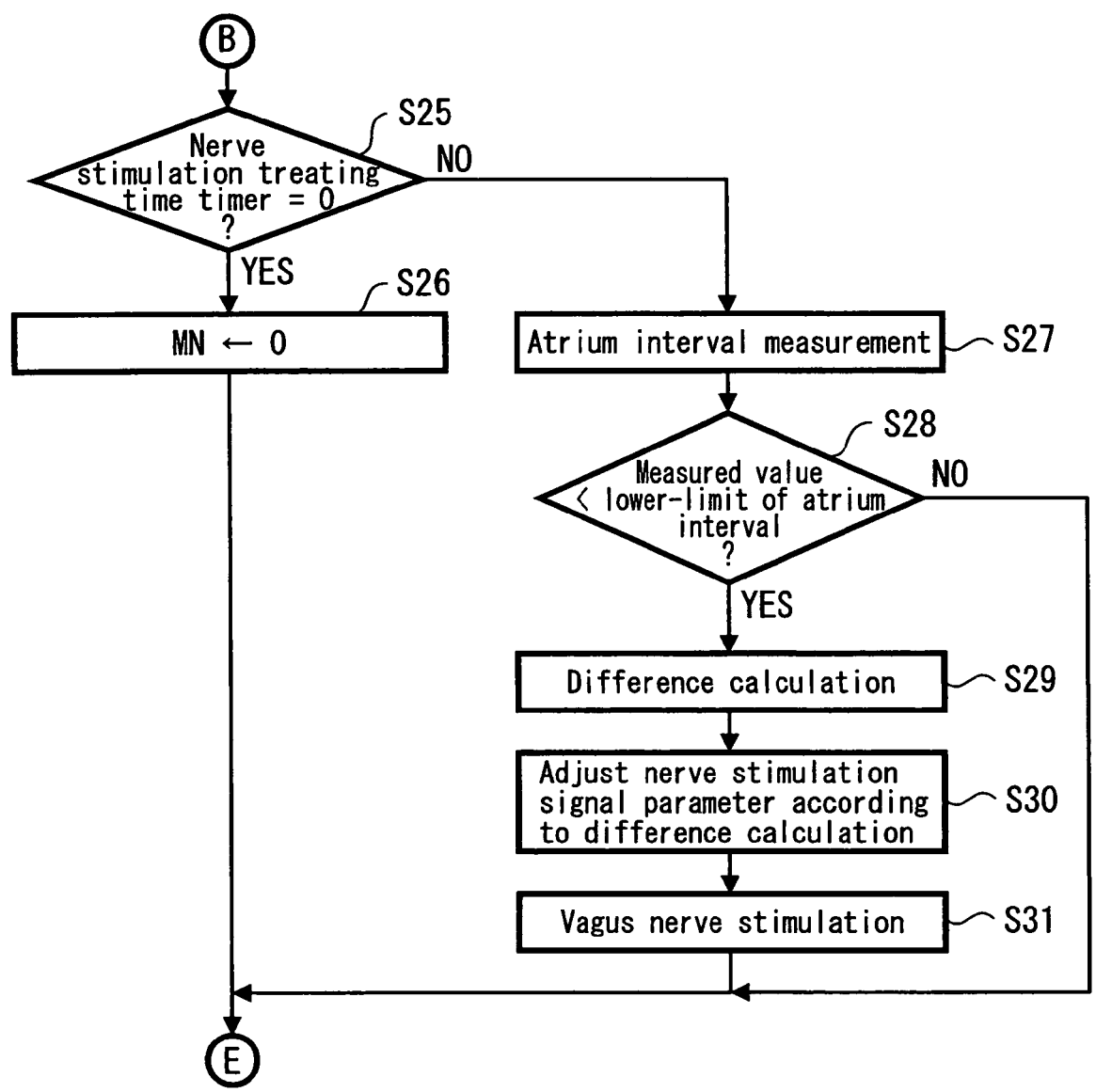
FIG. 5 is a portion of a flow diagram for explaining operation of the first exemplified embodiment according to the heart treatment apparatus of the present invention.

Next, the operation in a case when the atrium contraction was detected in judgment step S8 of FIG. 3 (after (B) of FIG. 3) will be explained according to a flow diagram of FIG. 5. When the atrium contraction is detected in judgment step S8 of FIG. 3, it is judged next whether or not the nerve stimulation treating time timer 14 became "0" (step S25). In a case when the nerve stimulation treating time timer 14 is "0", more specifically, when there becomes no output from the nerve stimulation treating time timer 14 to the comparator unit 22 and the comparator unit 22 becomes in a non-operating state, the maximum precursor number MN is made to be "0" (step S26) and the flow returns to (E) of the flow diagram in FIG. 3.

When the nerve stimulation treating time timer 14 is not "0" in judgment step S25, more specifically, when the nerve stimulation treatment is in an activation state, the interval of the atrium event detected by the atrium interval measuring unit 17 is measured (step S27).

Then, it is judged whether or not this atrium interval measured value is shorter than the lower-limit of the atrium interval selected by the atrium interval lower-limit table memory unit 21 (step S28).

Figure 3:
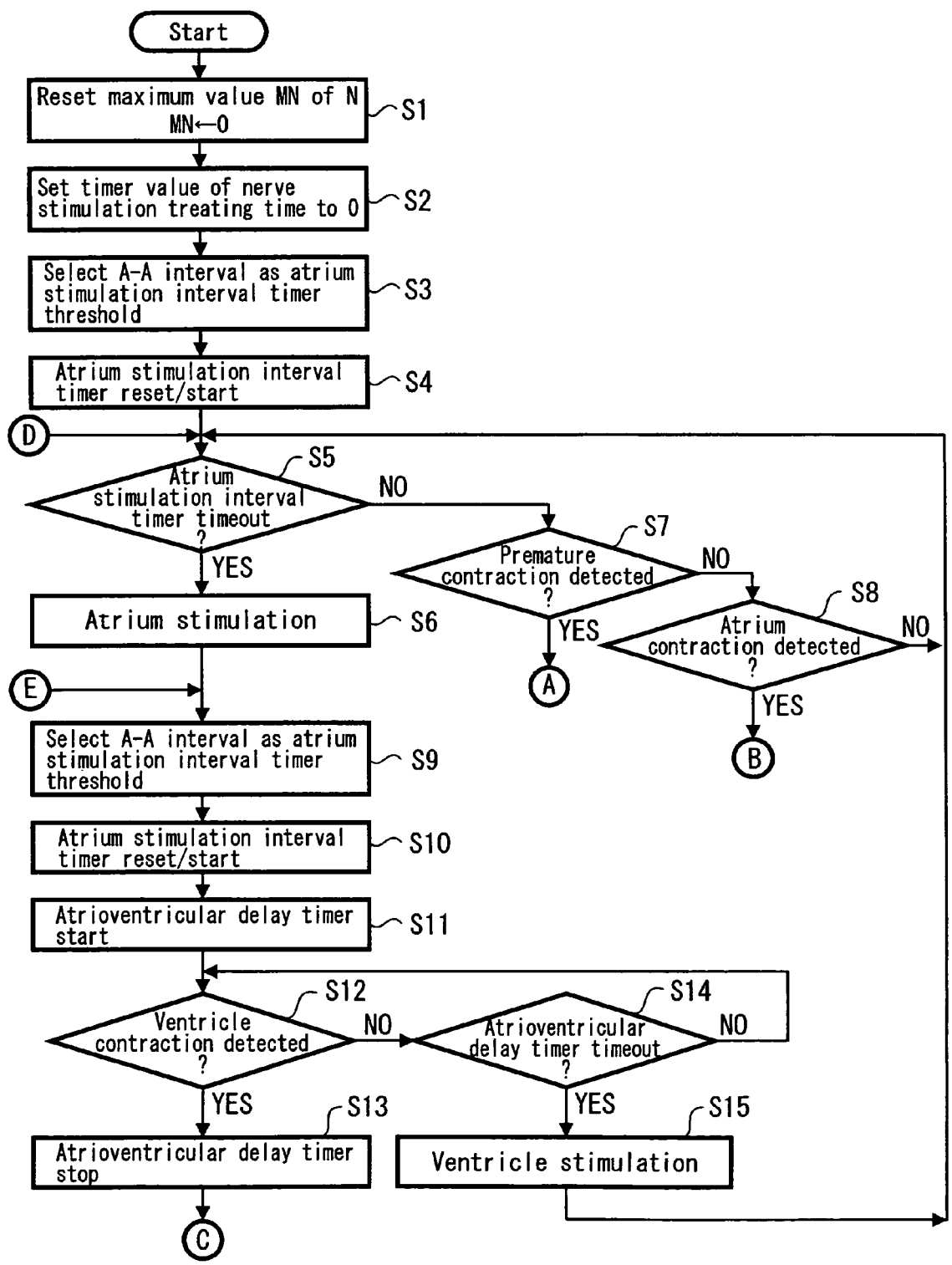
FIG. 3 is a portion of a flow diagram for explaining operation of the first exemplified embodiment according to the heart treatment apparatus of the present invention.

When the measured value of the atrium interval measuring unit 17 is longer than or equal to the lower-limit of the atrium interval in the judgment step S28, the stimulation of the vagus nerve 35 is not carried out and the flow returns to (E) of FIG. 3. When the measured value of the atrium interval measuring unit 17 is shorter than the lower-limit of the atrium interval, difference between the measured value and the lower-limit of the atrium interval is calculated in the difference calculation unit 23 (step S29). Then, the calculated difference is added to the nerve stimulation signal control unit 25, a nerve stimulation signal parameter is selected and degree of the nerve stimulation is adjusted (step S30). This nerve stimulation signal parameter is transmitted from the nerve stimulation signal control unit 25 to the nerve stimulation unit 6 and nerve stimulation is carried out in response to the parameter (step S31). After the nerve stimulation was carried out, the flow returns to (E) of FIG. 3.

Next, the operation flow subsequent to step S13 of FIG. 3 will be explained according to a flow diagram of FIG. 6. As shown in the flow diagram of FIG. 3, when the ventricle contraction is detected (step S12) and the clocking of the atrioventricular delay timer 18 stops, the flow proceeds to (C) of FIG. 6 and it is judged whether or not precursor was detected in the ventricle tachyarrhythmia precursor detection unit 7 (step S32). It should be noted that detection of the premature contraction is carried out in judgment step S7 of FIG. 3, so that it is judged here whether or not precursor other than premature contraction such as repolarization abnormality, ST change or the like was detected.

When precursor other than premature contraction is detected, a precursor number N corresponding to the precursor is obtained (step S33) and it is judged whether or not the precursor number N is smaller than the maximum precursor number MN (step S34). When the precursor number N is bigger than or equal to the maximum precursor number MN, the obtained precursor number N is made to be the maximum precursor number MN (step S35). Then, a corresponding lower-limit of the atrium interval is selected from the atrium interval lower-limit table memory unit 21 according to the precursor number N (step S36) and at the same time, a corresponding nerve stimulation treating time is selected in the nerve stimulation treating time table memory unit 13 (step S37).

Then, the nerve stimulation treating time selected in the nerve stimulation treating time table memory unit 13 is loaded to the nerve stimulation treating time timer 14 (step S38) and the nerve stimulation treating time timer 14 is made to start (step S39).

When precursor other than premature contraction was not detected in judgment step S32, when the precursor number N is smaller than the maximum precursor number MN in judgment step S34 or after the nerve stimulation treating time timer 14 starts in step S39, the flow returns to (D) of FIG. 3 in any case thereof and it is judged whether or not the atrium stimulation interval timer 8 was timeout.

Next, a second exemplified embodiment of the heart treatment apparatus of the present invention will be explained according to a block diagram of FIG. 7. The same constitutional portions as those of the first exemplified embodiment shown in FIG. 1 are shown by the same reference numerals.

Figure 7:
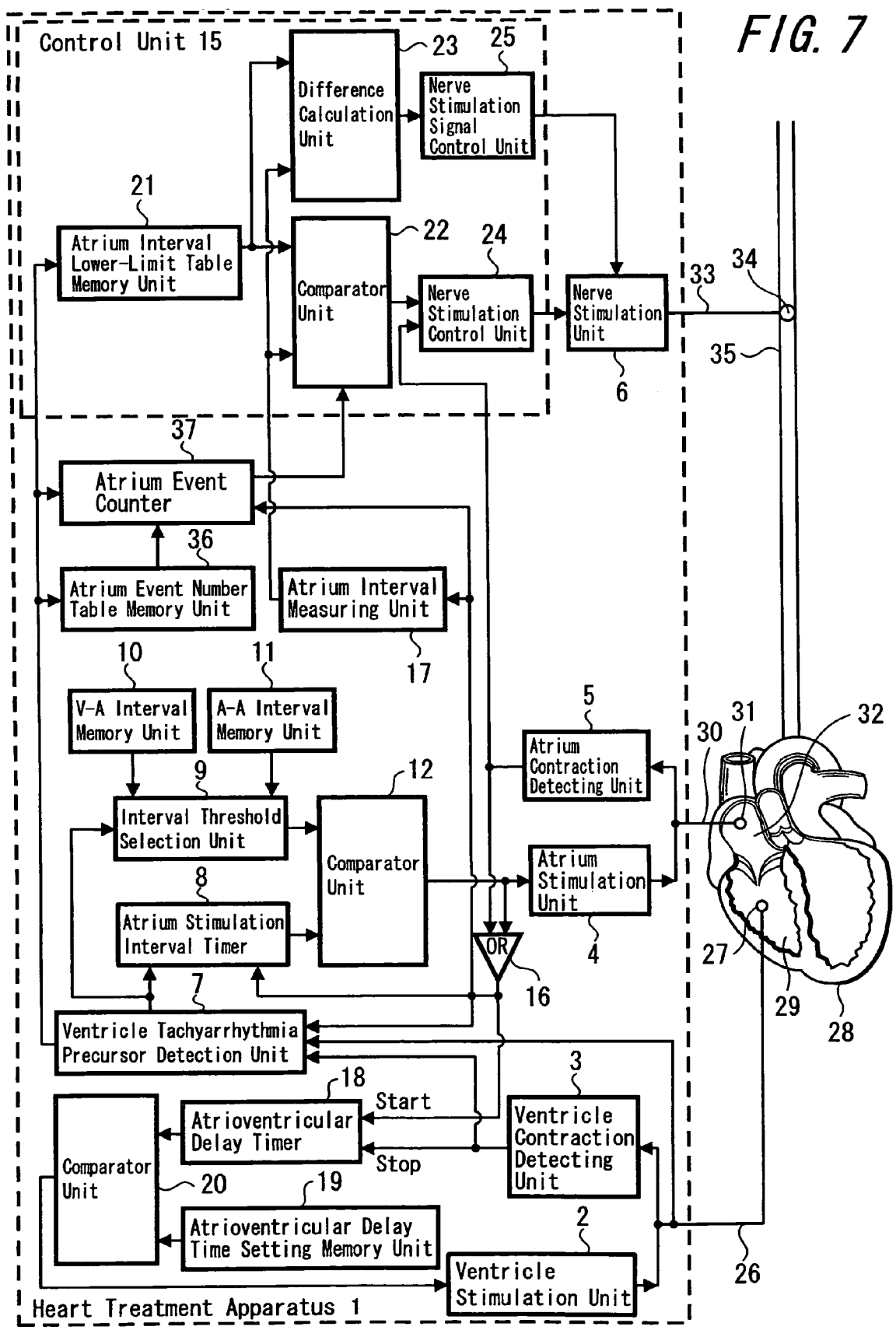
FIG. 7 is a block diagram showing a second exemplified embodiment according to the heart treatment apparatus of the present invention.

In the block diagram of FIG. 7, the constitutional portion different from that of the first exemplified embodiment in FIG. 1 is a portion in which an atrium event number table memory unit 36 and an atrium event counter 37 of FIG. 7 are provided instead of the nerve stimulation treating time table memory unit 13 and the nerve stimulation treating time timer 14 of FIG. 1.

In the second exemplified embodiment of the present invention, when precursor is detected by the ventricle tachyarrhythmia precursor detection unit 7, a precursor number N corresponding to the precursor is supplied to the atrium event number table memory unit 36 and the atrium event counter 37. Then, in the atrium event number table memory unit 36, as shown in table 3, the number of times of the atrium event corresponding to the precursor number N is selected among the number of times of the atrium event AEN1 to AEN4. Then, the number of times of the atrium event is loaded to the atrium event counter 37.

The values of AEN1 to AEN4 are to be set similarly as the nerve stimulation treating times or the lower-limits of the atrium interval by a medical doctor according to a clinical state or a clinical history of a patient and alternatively according to a result of an electrophysiologic test or the like and they are usually set such that the larger the precursor number N becomes, that is, the higher the risk of the tachyarrhythmia occurrence becomes, the larger they become.

TABLE 3

| precursor number (N) | precursor | number of times of atrium event | lower limit of atrium interval |
|---|---|---|---|
| 0 | none | — | — |
| 1 | single PVC | AEN1 | AAI1 |
| 2 | two successive PVC's <Couplet> | AEN2 | AAI1 |
| 3 | three or more successive | AEN3 | AAI1 |

TABLE 3-continued

| precursor number (N) | precursor | number of times of atrium event | lower limit of atrium interval |
|---|---|---|---|
| 4 | PVC's <Short-run> repolarization abnormality PVC <R on T> ST Increase ST Decrease | AEN4 | AAI1 |

(Control Example of Number of Times of Atrium event: AEN1 < AEN2 < AEN3 < AEN4)

Relation Between Ventricle Tachyarrhythmia Precursor and Number of Times of Atrium Event or Lower-Limit of Atrium Interval An output of the atrium event counter 37 is supplied to the comparator unit 22 of the control unit 15 and the comparator unit 22 is activated until the loaded number of times of the atrium event becomes "0" so as to make a state in which the nerve stimulation is possible. Then, the atrium event counter 37 operates as a down-counter and decrements the number of times of the atrium event which was loaded every time when the output of the OR circuit 16, that is, the atrium event is supplied. As this result, when the atrium event is detected as much as the loaded number of times of the atrium event from the OR circuit 16, the output from the atrium event counter 37 to the comparator unit 22 becomes in an OFF state and the comparator unit 22 is made to be in a non-operating state.

Hereinafter, the operation of the second exemplified embodiment of the present invention will be explained in detail according to flow diagrams of FIG. 8 to FIG. 11. There are many repetitive portions with the explanation of the operation of the first exemplified embodiment shown in FIG. 3 to FIG. 6, but the reference numerals of the steps are changed here and the whole flow diagram will be explained all there-through.

First, as for an operation of an initial state, the maximum value MN of the precursor number N is reset to "0" in the ventricle tachyarrhythmia precursor detection unit 7 (step S50). Next, the counted value AEN of the atrium event counter 37 is reset to "0" (step S51) and at the same time, the A-A interval stored in the A-A interval memory unit 11 is selected by the interval threshold selection unit 9 as the threshold of the atrium stimulation interval timer 8 (step S52). Then, the atrium stimulation interval timer 8 is reset (step S53).

Next, it is judged whether or not the atrium stimulation interval timer 8 is timeout (step S54). In a case when the atrium stimulation interval timer 8 is timeout, the comparator unit 12 emanates an output and atrium stimulation is carried out by the atrium stimulation unit 4 (step S55), when the atrium stimulation interval timer 8 is not timeout, it is judged subsequently whether or not premature contraction was detected in the ventricle tachyarrhythmia precursor detection unit 7 (step S56).

Figure 9:
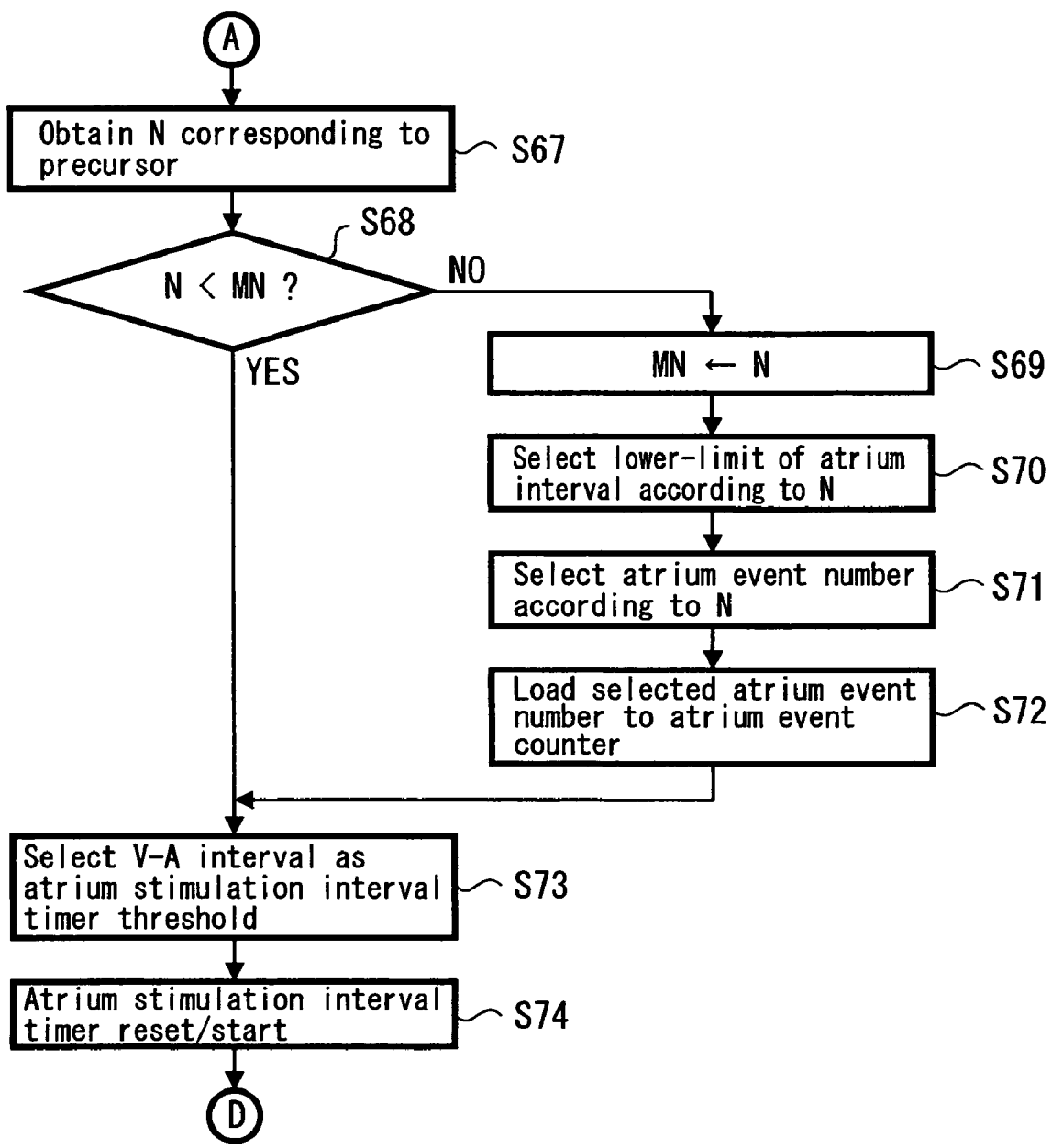
FIG. 9 is a portion of a flow diagram for explaining operation of the second exemplified embodiment according to the heart treatment apparatus of the present invention.

In a case when the premature contraction is detected in judgment step S56, the flow proceeds to (A) of FIG. 9 and when the premature contraction is not detected, it is judged subsequently whether or not atrium contraction was detected in the atrium contraction detecting unit 5 (step S57). In a case when the atrium contraction is detected, the flow proceeds to (B) of FIG. 10 and in a case when the atrium contraction is not detected, the flow returns to judgment step S54 and it is judged whether or not the atrium stimulation interval timer 8 was timeout.

Figure 11:
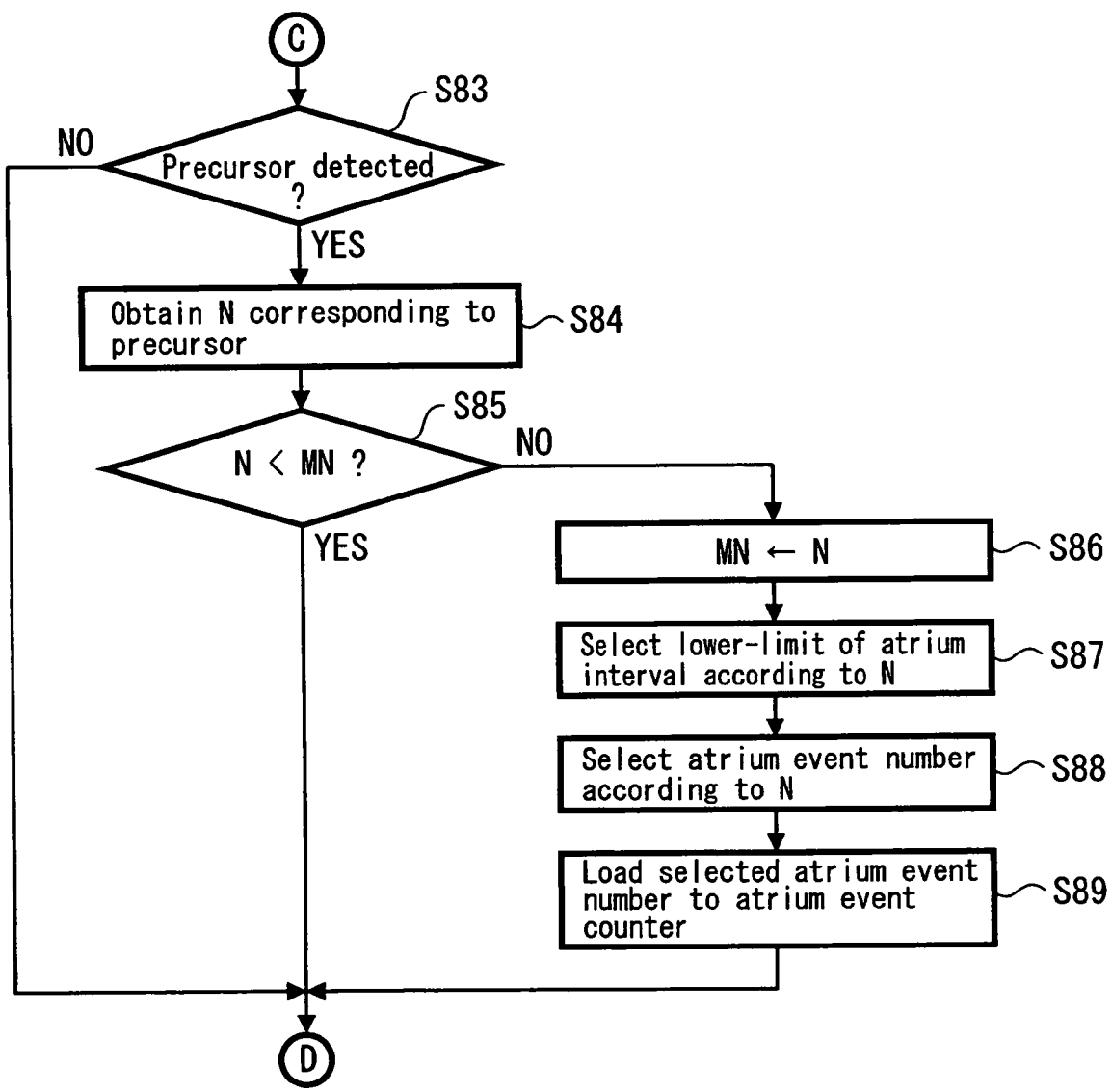
FIG. 11 is a portion of a flow diagram for explaining operation of the second exemplified embodiment according to the heart treatment apparatus of the present invention.

After the atrium stimulation was carried out in step S55, it is judged whether or not the counted value AEN of the atrium event counter 37 is "0" (step S58). "0" is introduced in step S51 with respect to the AEN and it is judged anew here, because (D) of FIG. 9 and FIG. 11 is feedback to the preceding stage of judgment step S54.

If AEN=0 is not true in judgment step S58, a numeric value subtracting "1" from AEN is made to be a new AEN (step S59) and If AEN=0 is true in judgment step S58, the flow proceeds to next by skipping step S59.

Then, in step S60, the A-A interval stored in the A-A interval memory unit 11 is again selected as the threshold of the atrium stimulation interval timer 8 and the atrium stimulation interval timer 8 is reset (step S61). Further, the clocking of the atrioventricular delay timer 18 is started (step S62).

Next, it is judged whether or not ventricle contraction was detected in the ventricle contraction detecting unit 3 (step S63). If the ventricle contraction is detected, the clocking of the atrioventricular delay timer 18 is stopped (step S64) and in a case when the ventricle contraction is not detected, it is judged whether or not the atrioventricular delay timer 18 is timeout, more specifically, whether or not the atrioventricular delay timer 18 made clocking beyond the set value stored in the atrioventricular delay time setting memory unit 19 (step S65). In a case when the atrioventricular delay timer 18 is not timeout, the flow returns to judgment step S63 and waits for ventricle contraction detection. When the atrioventricular delay timer 18 is timeout, the comparator unit 20 emanates an output to the ventricle stimulation unit 2 and stimulation of the right ventricle 29 of the heart 28 is carried out by the ventricle stimulation electrode 27 (step S66). Subsequently, the flow returns to judgment step S54 and it is judged whether or not the atrium stimulation interval timer 8 was timeout.

Next, operations after the premature contraction is detected in judgment step S56 (after (A) of FIG. 8) will be explained according to a flow diagram of FIG. 9. When the premature contraction is detected in judgment step S56 of FIG. 8, the flow proceeds to (A) OF FIG. 9 and the precursor number N corresponding to the precursor is obtained in the ventricle tachyarrhythmia precursor detection unit 7 (step S67). For example, in a case when the single premature contraction is caused, N=1 is made as shown in table 2 and this is registered as a precursor number in the ventricle tachyarrhythmia precursor detection unit 7.

Next, the obtained precursor number N is compared with the maximum precursor number MN (step S68). In step S50 of FIG. 8, the maximum symptom number MN is set to "0", but (D) of FIG. 9 and FIG. 11 is supplied to the preceding stage of judgment step S54 in the flow diagram of FIG. 8, so that there is a case in which MN is not smaller than N.

When the precursor number N is not smaller than MN in judgment step S68, that is, when MN≦N is true, the value of MN is replaced by the value of N (step S69). Subsequently, the lower-limit of the atrium interval stored in the atrium interval lower-limit table memory unit 21 is selected according to the detected precursor number N (step S70) and further, the atrium event number of times stored in the atrium event number table memory unit 36 is selected according to the precursor number N (step S71). Then, aforesaid selected atrium event number of times is loaded to the atrium event counter 37 (step S72).

When the precursor number N is smaller than the maximum precursor number MN in judgment step S68 and after the atrium event number of times was loaded to the atrium event counter 37 in step S72, the interval threshold selection unit 9 selects the V-A interval stored in the V-A interval memory unit 10 as the threshold of the atrium stimulation interval timer 8 (step S73). Then at the same time, the atrium stimulation interval timer 8 is reset and the clocking is started (step S74). Thereafter, the flow returns to (D) of FIG. 8.

Figure 10:
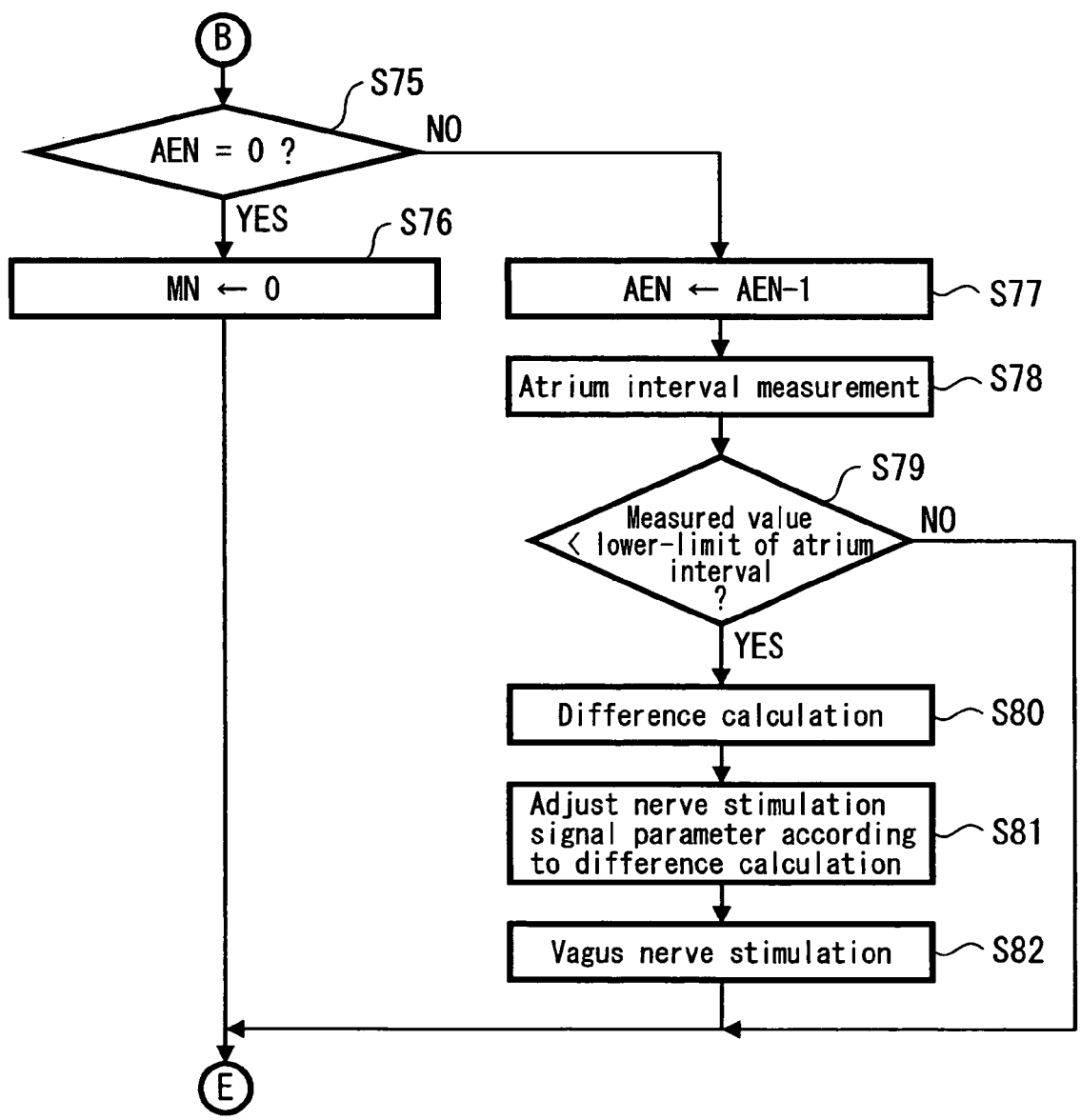
FIG. 10 is a portion of a flow diagram for explaining operation of the second exemplified embodiment according to the heart treatment apparatus of the present invention.

Next, the operation in a case when the atrium contraction was detected in judgment step S57 of FIG. 8 (after (B) of FIG. 8) will be explained according to a flow diagram of FIG. 10. When the atrium contraction is detected in judgment step S57 of FIG. 8, it is judged whether or not the atrium event number of times AEN loaded in the atrium event counter 37 is "0" (step S75). In a case when the atrium event number of times AEN=0 is true, more specifically, in a case when the nerve stimulation treatment period was ended, the maximum precursor number MN is made to be "0" (step S76) and the flow returns to (E) of the flow diagram in FIG. 8.

When AEN loaded in the atrium event counter 37 is not "0" in judgment step S75, more specifically, when the nerve stimulation treatment is in an activation state, "1" is decremented from the stored atrium event number of times in the atrium event counter 37 every time on an occasion of the atrium event detection (step S77). Then, the atrium event interval detected by the atrium interval measuring unit 17 is measured (step S78).

Next, it is judged whether or not this atrium interval measured value is shorter than the lower-limit of the atrium interval selected by the atrium interval lower-limit table memory unit 21 (step S79). Here, when the measured value of the atrium interval measuring unit 17 is longer than or equal to the lower-limit of the atrium interval, the stimulation of the vagus nerve 35 is not carried out and the flow returns to (E) of FIG. 8. Then, when the measured value of the atrium interval measuring unit 17 is shorter than the lower-limit of the atrium interval, difference between the measured value and the lower-limit of the atrium interval is calculated in the difference calculation unit 23 (step S80). The calculated difference is supplied to the nerve stimulation signal control unit 25, a nerve stimulation signal parameter is selected and degree of the nerve stimulation is adjusted (step S81). This nerve stimulation signal parameter is transmitted from the nerve stimulation signal control unit 25 to the nerve stimulation unit 6 and nerve stimulation is carried out in response to the parameter (step S82). After the nerve stimulation was carried out, the flow returns to (E) of FIG. 8.

Next, the operation flow subsequent to step S64 of FIG. 8 will be explained according to a flow diagram of FIG. 11. As shown in the flow diagram of FIG. 8, when the ventricle contraction is detected (step S63) and the clocking of the atrioventricular delay timer 18 stops, the flow proceeds to (C) of FIG. 11 and it is judged whether or not precursor was detected in the ventricle tachyarrhythmia precursor detection unit 7 (step S83). It should be noted that detection of the premature contraction is carried out in judgment step S56 of FIG. 8, so that it is judged here whether or not precursor other than premature contraction such as repolarization abnormality, ST change or the like was detected.

When precursor other than premature contraction is detected, a precursor number N corresponding to the precursor is obtained (step S84) and it is judged whether or not the precursor number N is smaller than the maximum precursor number MN (step S85). When the precursor number N is bigger than or equal to the maximum precursor number MN, the obtained precursor number N is made to be the maximum precursor number MN (step S86). Then, a corresponding lower-limit of an atrium interval is selected from the atrium interval lower-limit table memory unit 21 according to the precursor number N (step S87) and at the same time, a corresponding atrium event number of times is selected in the atrium event number table memory unit 36 (step S88).

Then, the atrium event number of times selected in the atrium event number table memory unit 36 is loaded to the atrium event counter 37 (step S89) and the nerve stimulation treatment by the control unit 15 is made to be in an active state during a period of the atrium event number of times loaded in the atrium event counter 37.

Figure 8:
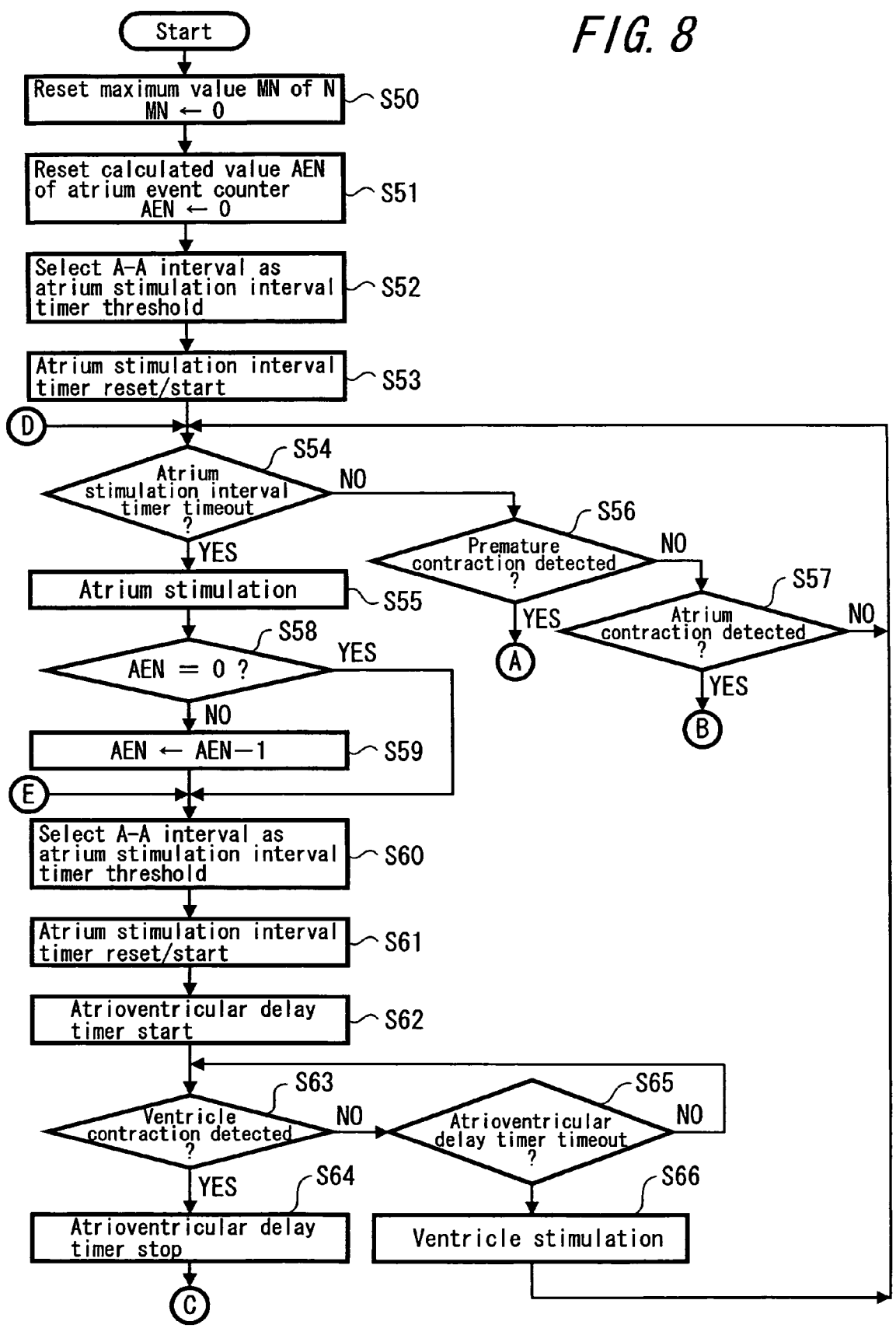
FIG. 8 is a portion of a flow diagram for explaining operation of the second exemplified embodiment according to the heart treatment apparatus of the present invention.

When precursor other than premature contraction was not detected in judgment step S83, when it is judged in judgment step S85 that the precursor number N is smaller than the maximum precursor number MN or after the atrium event number of times is loaded in the atrium event counter 37 in step S89, the flow returns to (D) of FIG. 8 in any case thereof and it is judged whether or not the atrium stimulation interval timer 8 was timeout.

Next, a third exemplified embodiment of the heart treatment apparatus of the present invention will be explained according to a block diagram of FIG. 12. The same constitutional portions as those of the first exemplified embodiment shown in FIG. 1 and the second exemplified embodiment shown in FIG. 7 are shown by the same reference numerals.

Figure 12:
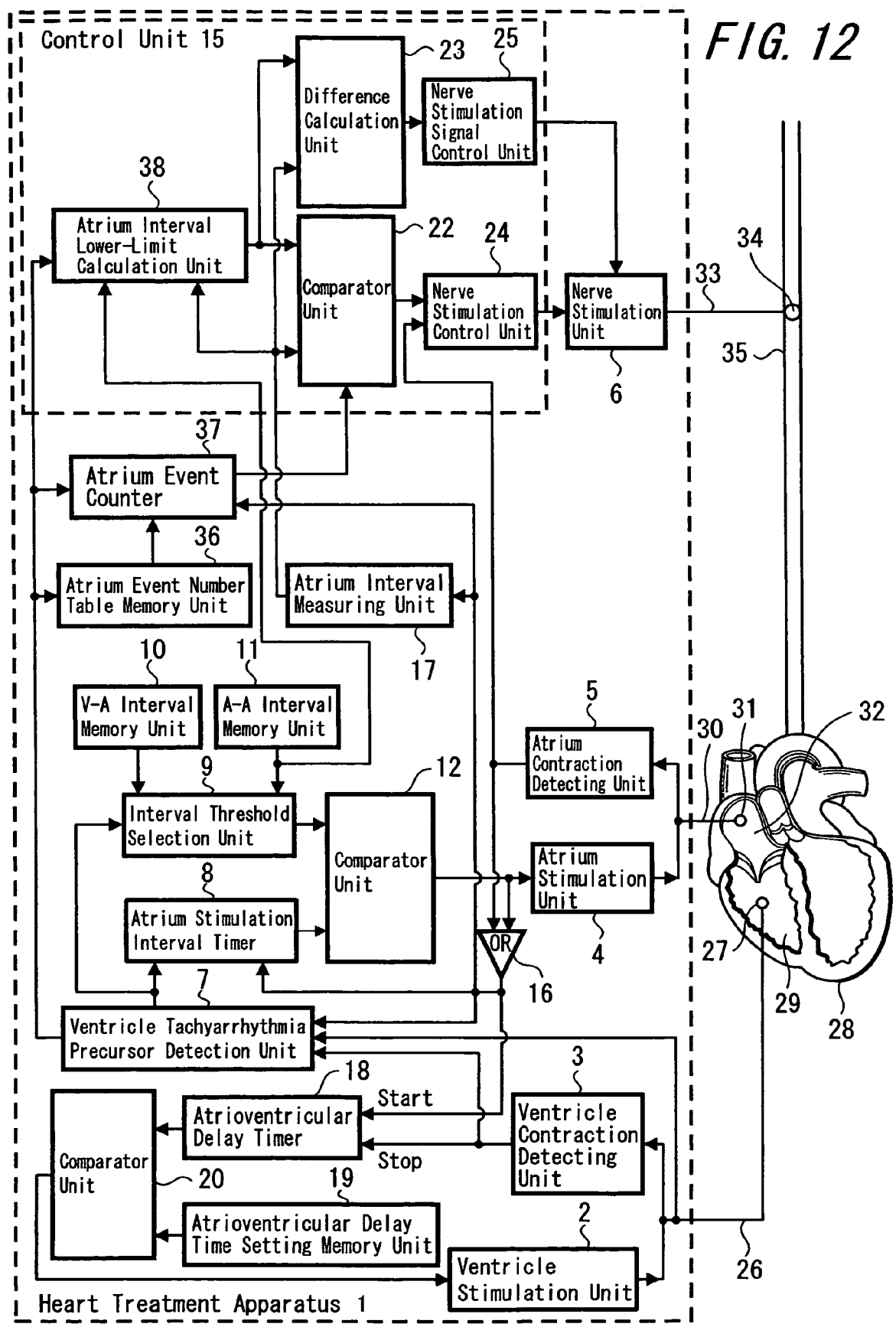
FIG. 12 is a block diagram showing a third exemplified embodiment according to the heart treatment apparatus of the present invention.

In the block diagram of FIG. 12, the constitutional portion different from that of the second exemplified embodiment shown in FIG. 7 lies in that an atrium interval lower-limit calculation unit 38 is provided instead of the atrium interval lower-limit table memory unit 21 of FIG. 7.

In the first exemplified embodiment and the second exemplified embodiment, when precursor of ventricle tachyarrhythmia is detected, a value which is set beforehand and is made to be correspondent with the detected precursor is selected as a threshold of the nerve stimulation for the lower-limit of the atrium interval which defined a lower limit of a permissible atrium interval range without relation to heart activity situation of a patient until that moment, but in the atrium interval lower-limit calculation unit 38 of the third exemplified embodiment, an atrium interval in advance of a precursor detection is maintained and this maintained atrium interval is added with a predetermined amount of an interval value so as to be set as the lower-limit of the atrium interval, so that the permissible atrium interval range is controlled depending on situation of a patient.

Figure 13:
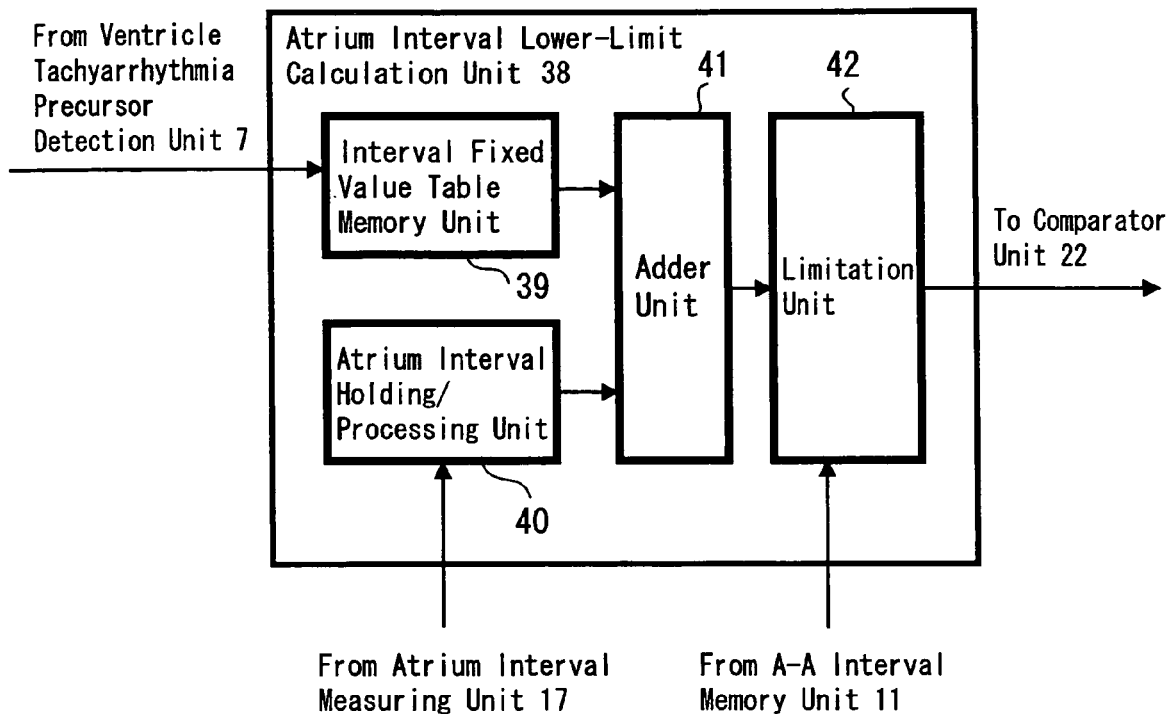
FIG. 13 is a block diagram showing one constitutional example of atrium interval lower-limit calculation means in the third exemplified embodiment according to the heart treatment apparatus of the present invention.
Figure 14:
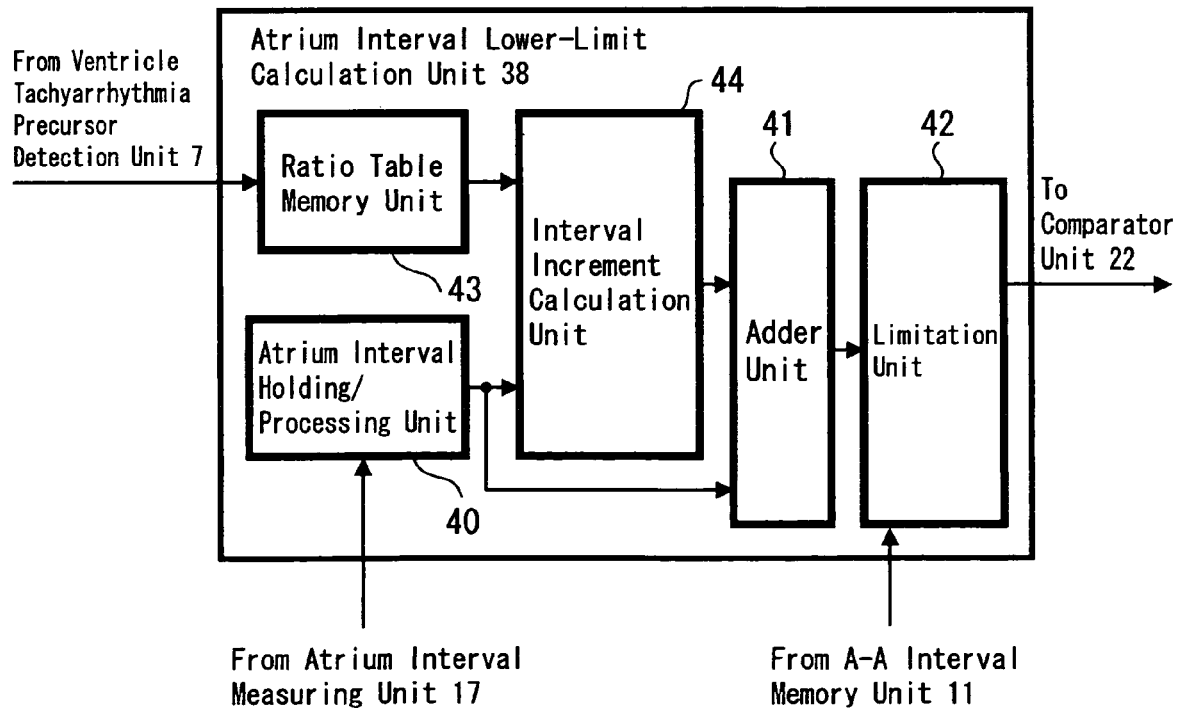
FIG. 14 is a block diagram showing another constitutional example of an atrium interval lower-limit calculation unit in the third exemplified embodiment according to the heart treatment apparatus of the present invention.

Examples of the atrium interval lower-limit calculation unit 38 are shown in FIG. 13 and FIG. 14. More specifically, in the example shown in FIG. 13, the atrium interval lower-limit calculation unit 38 is constituted by an interval fixed value table memory unit 39 supplied with a precursor number N from the ventricle tachyarrhythmia precursor detection unit 7, an atrium interval holding/processing unit 40 supplied with a measured value from the atrium interval measuring unit 17, an adder unit 41 for adding an interval fixed value stored in the aforesaid interval fixed value table memory unit 39 to the atrium interval which is a measured value stored and maintained in the atrium interval holding/processing unit 40, and a limitation unit 42 for limiting the output of the adder unit 41 according to the output of the A-A interval memory unit 11.

Next, it will be explained with respect to the operation of the atrium interval lower-limit calculation unit 38 which is constituted in such a manner and shown in FIG. 13.

When the precursor number N from the ventricle tachyarrhythmia precursor detection unit 7 is applied to the interval fixed value table memory unit 39, the interval fixed value table memory unit 39 selects an interval fixed value according to the precursor number N among a plurality of interval fixed values. Also, the atrium interval holding/processing unit 40 receives the atrium interval measured value from the atrium interval measuring unit 17 and maintains that and the maintained measured value and the interval fixed value selected in the interval fixed value table memory unit 39 are added by the adder unit 41. Then, in the limitation unit 42, the A-A interval from the A-A interval memory unit 11 and the calculated lower-limit of the atrium interval added in aforesaid adder unit 41 are compared, and the calculated lower-limit of the atrium interval is limited so as to be equal to or less than the A-A interval and is transmitted to the comparator unit 22.

Also, the atrium interval lower-limit calculation unit 38 shown in FIG. 14 is provided with a ratio table memory unit 43 and an interval increment calculation unit 44 instead of the interval fixed value table memory unit 39 of FIG. 13.

The operation of the atrium interval lower-limit calculation unit 38 in this FIG. 14 will be explained. First, when precursor is detected by the ventricle tachyarrhythmia precursor detection unit 7, a precursor number N corresponding to that precursor is supplied to the ratio table memory unit 43. The ratio table memory unit 43 sets the ratio for adding to the detected atrium interval in response to the precursor number N and transmits it to the interval increment calculation unit 44. Also, the atrium interval holding/processing unit 40 receives the atrium interval measured value from the atrium interval measuring unit 17, maintains it and transmits this maintained measured value to the interval increment calculation unit 44 and the adder unit 41.

The interval increment calculation unit 44 multiplies the ratio (percent) set by the ratio table memory unit 43 and the atrium interval stored in the atrium interval holding/processing unit 40, calculates the interval increment and transmits that to the adder unit 41.

The adder unit 41 adds the atrium interval stored in the atrium interval holding/processing unit 40 and the interval increment calculated by aforesaid interval increment calculation unit 44 and supplies that to the limitation unit 42. Then, the operation of the limitation unit 42 is same as that in FIG. 13.

Hereinafter, the operation of the third exemplified embodiment of the present invention will be explained in detail according to flow diagrams of FIG. 15 to FIG. 18. There are many repetitive portions with the operation flow diagram of the first exemplified embodiment shown in FIG. 3 to FIG. 6 or the operation flow diagram of the second exemplified embodiment shown in FIG. 8 to FIG. 11, but the reference numerals of the steps are changed here and the whole flow diagram will be explained all there-through.

Figure 15:
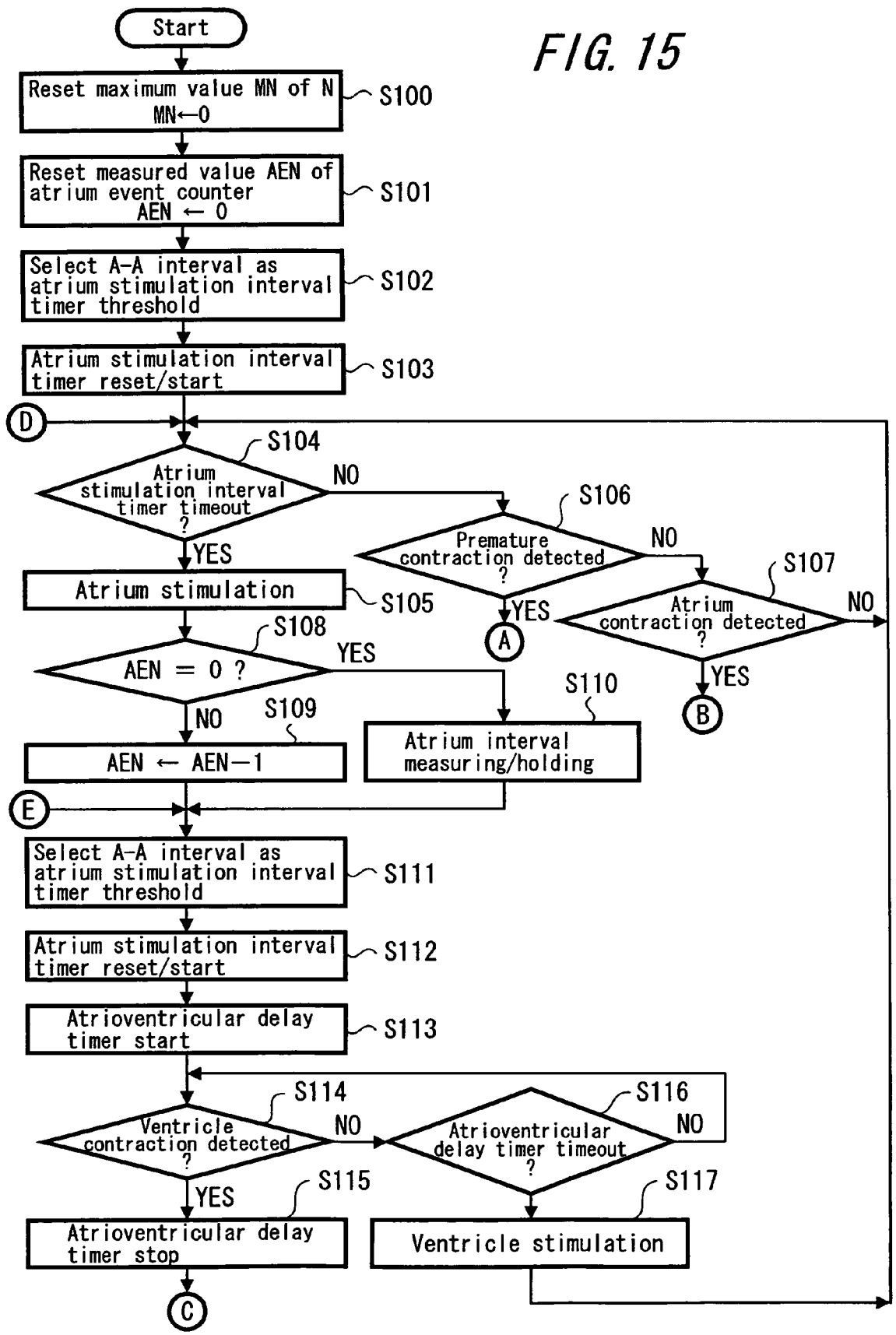
FIG. 15 is a portion of a flow diagram for explaining operation of the third exemplified embodiment according to the heart treatment apparatus of the present invention.

First, in FIG. 15, as for an operation of an initial state, the maximum value MN of the precursor number N is reset to "0" in the ventricle tachyarrhythmia precursor detection unit 7 (step S100). Next, the measured value of the atrium event counter 37 is set to "0" (step S101) and at the same time, the A-A interval stored in the A-A interval memory unit 11 is selected by the interval threshold selection unit 9 as the threshold of the atrium stimulation interval timer 8 (step S102) Then, the atrium stimulation interval timer 8 is reset and started (step S103).

Next, it is judged whether or not the atrium stimulation interval timer 8 is timeout (step S104). In a case when the atrium stimulation interval timer 8 is timeout, the comparator unit 12 emanates an output and atrium stimulation is carried out by the atrium stimulation unit 4 (step S105), when the atrium stimulation interval timer 8 is not timeout, it is judged subsequently whether or not premature contraction was detected in the ventricle tachyarrhythmia precursor detection unit 7 (step S106).

Figure 16:
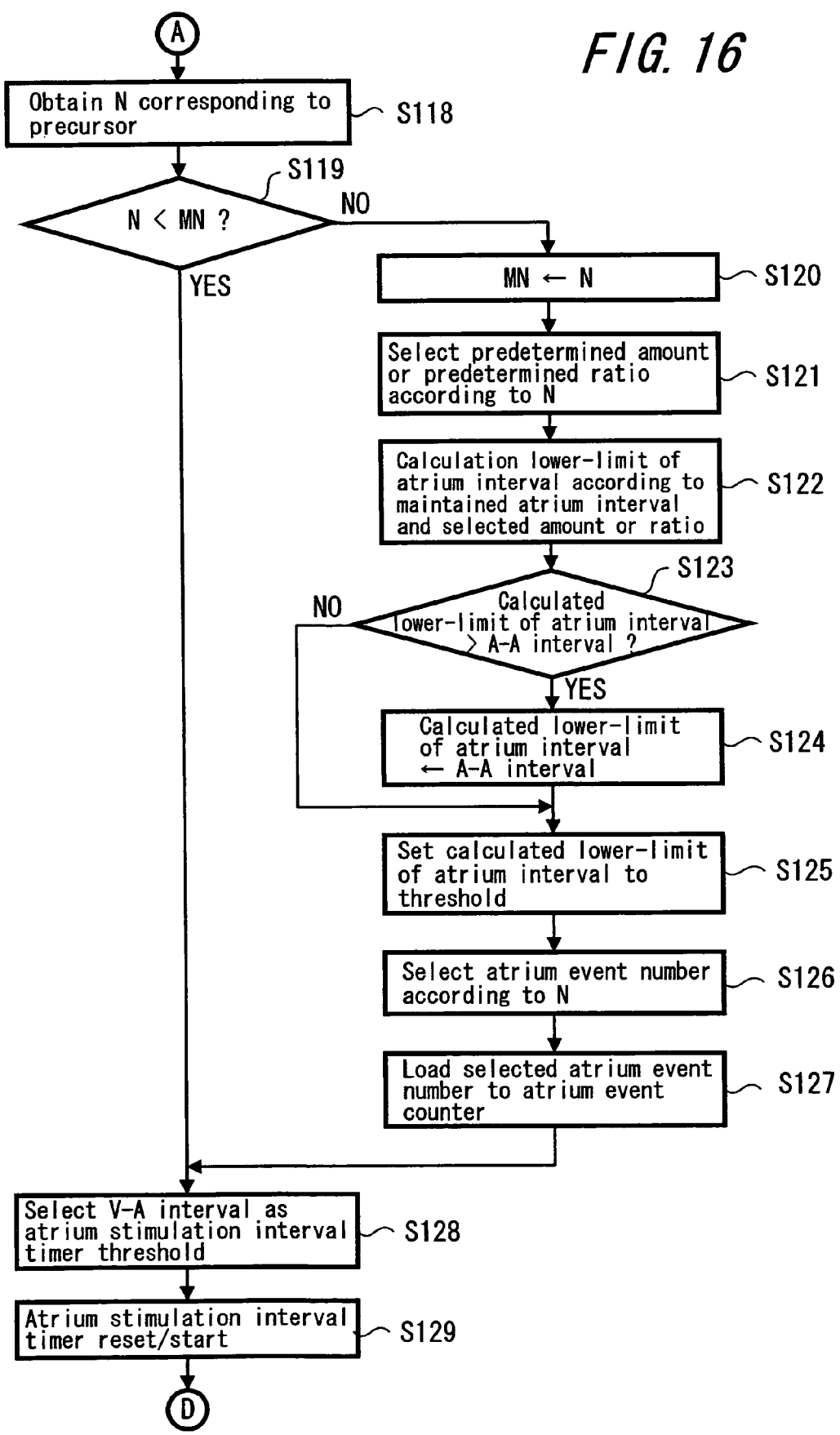
FIG. 16 is a portion of a flow diagram for explaining operation of the third exemplified embodiment according to the heart treatment apparatus of the present invention.

In a case when the premature contraction is detected in judgment step S106, the flow proceeds to (A) of FIG. 16 and when the premature contraction is not detected, it is judged subsequently whether or not atrium contraction was detected in the atrium contraction detecting unit 5 (step S107). In a case when the atrium contraction is detected, the flow proceeds to (B) of FIG. 17 and in a case when the atrium contraction is not detected, the flow returns to judgment step S104 and it is judged whether or not the atrium stimulation interval timer 8 was timeout.

Figure 18:
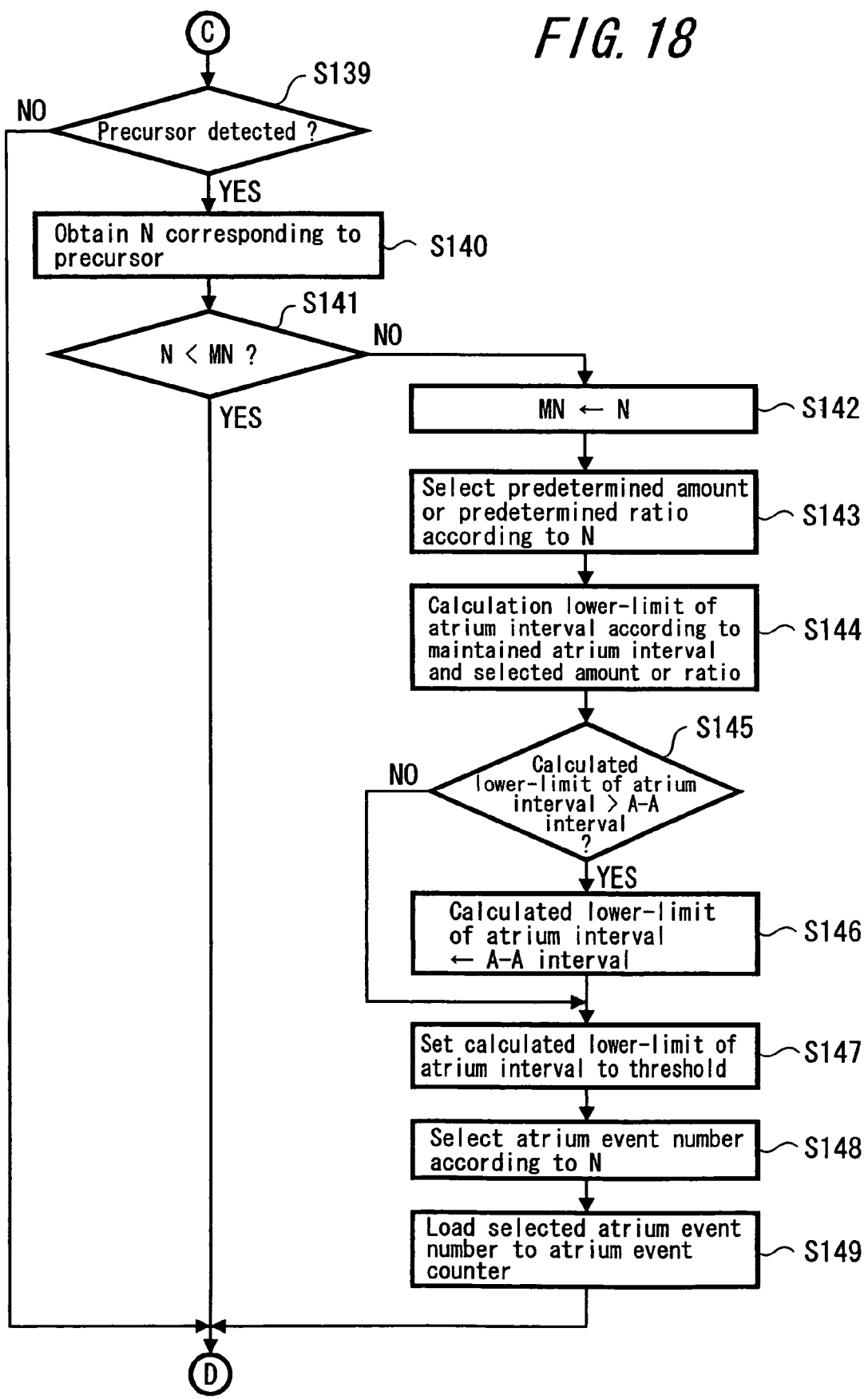
FIG. 18 is a portion of a flow diagram for explaining operation of the third exemplified embodiment according to the heart treatment apparatus of the present invention.

After the atrium stimulation was carried out in step S105, it is judged whether or not the counted value AEN of the atrium event counter 37 is "0" (step S108). "0" is introduced in step S101 with respect to the AEN and it is judged anew here, because (D) of FIG. 16 and FIG. 18 is feedback to the preceding stage of judgment step S104.

If AEN=0 is not true in judgment step S108, a numeric value subtracting "1" from AEN is made to be a new AEN (step S109) and If AEN=0 is true in judgment step S108, the atrium interval measured value measured by the atrium interval measuring unit 17 is stored in the atrium interval holding/processing unit 40 of the atrium interval lower-limit calculation unit 38 and maintained (step S110).

Then, in step S111, the A-A interval stored in the A-A interval memory unit 11 is again selected as the threshold of the atrium stimulation interval timer 8 and the atrium stimulation interval timer 8 is reset (step S112). Further, the clocking of the atrioventricular delay timer 18 is started (step S113).

Next, it is judged whether or not ventricle contraction was detected in the ventricle contraction detecting unit 3 (step S114). If the ventricle contraction is detected, the clocking of the atrioventricular delay timer 18 is stopped (step S115) and in a case when the ventricle contraction is not detected, it is judged whether or not the atrioventricular delay timer 18 is timeout, more specifically, whether or not the atrioventricular delay timer 18 made clocking beyond the set value stored in the atrioventricular delay time setting memory unit 19 (step S116) In a case when the atrioventricular delay timer 18 is not timeout, the flow returns to judgment step S114 and waits for ventricle contraction detection. When the atrioventricular delay timer 18 is timeout, the comparator unit 20 emanates an output to the ventricle stimulation unit 2 and stimulation of the right ventricle 29 of the heart 28 is carried out by the ventricle stimulation electrode 27 (step S117). Subsequently, the flow returns to judgment step S104 and it is judged whether or not the atrium stimulation interval timer 8 was timeout.

Next, operations after the premature contraction is detected in judgment step S106 (after (A) of FIG. 15) will be explained according to a flow diagram of FIG. 16. When the premature contraction is detected in judgment step S106 of FIG. 15, the flow proceeds to (A) OF FIG. 16 and the precursor number N corresponding to the precursor is obtained in the ventricle tachyarrhythmia precursor detection unit 7 (step S118). For example, in a case when the single premature contraction is caused, N=1 is made as shown in table 3 and this is registered as a precursor number in the ventricle tachyarrhythmia precursor detection unit 7.

Next, the obtained precursor number N is compared with the maximum precursor number MN (step S119). Here, in step S100 of FIG. 15, the maximum symptom number MN is set to "0", but (D) of FIG. 16 and FIG. 18 is supplied to the preceding stage of judgment step S104 in the flow diagram of FIG. 15, so that there is a case in which MN is not smaller than N.

When N is not smaller than MN in judgment step S119, that is, when MN≦N is true, the value of MN is replaced by the value of N (step S120). Subsequently, in the atrium interval lower-limit calculation unit 38, a predetermined amount (case of FIG. 13) or a predetermined ratio (case of FIG. 14) with respect to the atrium interval measured by the atrium interval measuring unit 7 is selected according to the detected precursor number N (step S121).

Then, the lower-limit of the atrium interval is calculated in the atrium interval lower-limit calculation unit 38 according to aforesaid selected predetermined amount or predetermined ratio and the atrium interval maintained in the atrium interval holding/processing unit 40 (step S122).

Next, in the limitation unit 42 of the atrium interval lower-limit calculation unit 38, the magnitude relation between this calculated lower-limit of the atrium interval and the A-A interval stored in the A-A interval memory unit 11 is compared (step S123). When the calculated lower-limit of the atrium interval is longer than the A-A interval, the calculated lower-limit of the atrium interval is replaced by the A-A interval (step S124) and when the calculated lower-limit of the atrium interval is equal to or shorter than the A-A interval, step S124 is skipped and the calculated lower-limit of the atrium interval is made to be the lower limit of the atrium interval threshold supplied to the comparator unit 22 (step S125).

Subsequently, the atrium event number of tiems stored in the atrium event number table memory unit 36 is selected according to the precursor number N (step S126). Then, aforesaid selected atrium event number of times is loaded to the atrium event counter 37 (step S127).

When the precursor number N is smaller than the maximum precursor number MN in judgment step S119 and after the atrium event number of times was loaded to the atrium event counter 37 in step S127, the interval threshold selection unit 9 selects the V-A interval stored in the V-A interval memory unit 10 as the threshold of the atrium stimulation interval timer 8 (step S128). Then at the same time, the atrium stimulation interval timer 8 is reset and the clocking is started (step S129) Thereafter, the flow returns to (D) of FIG. 15.

Figure 17:
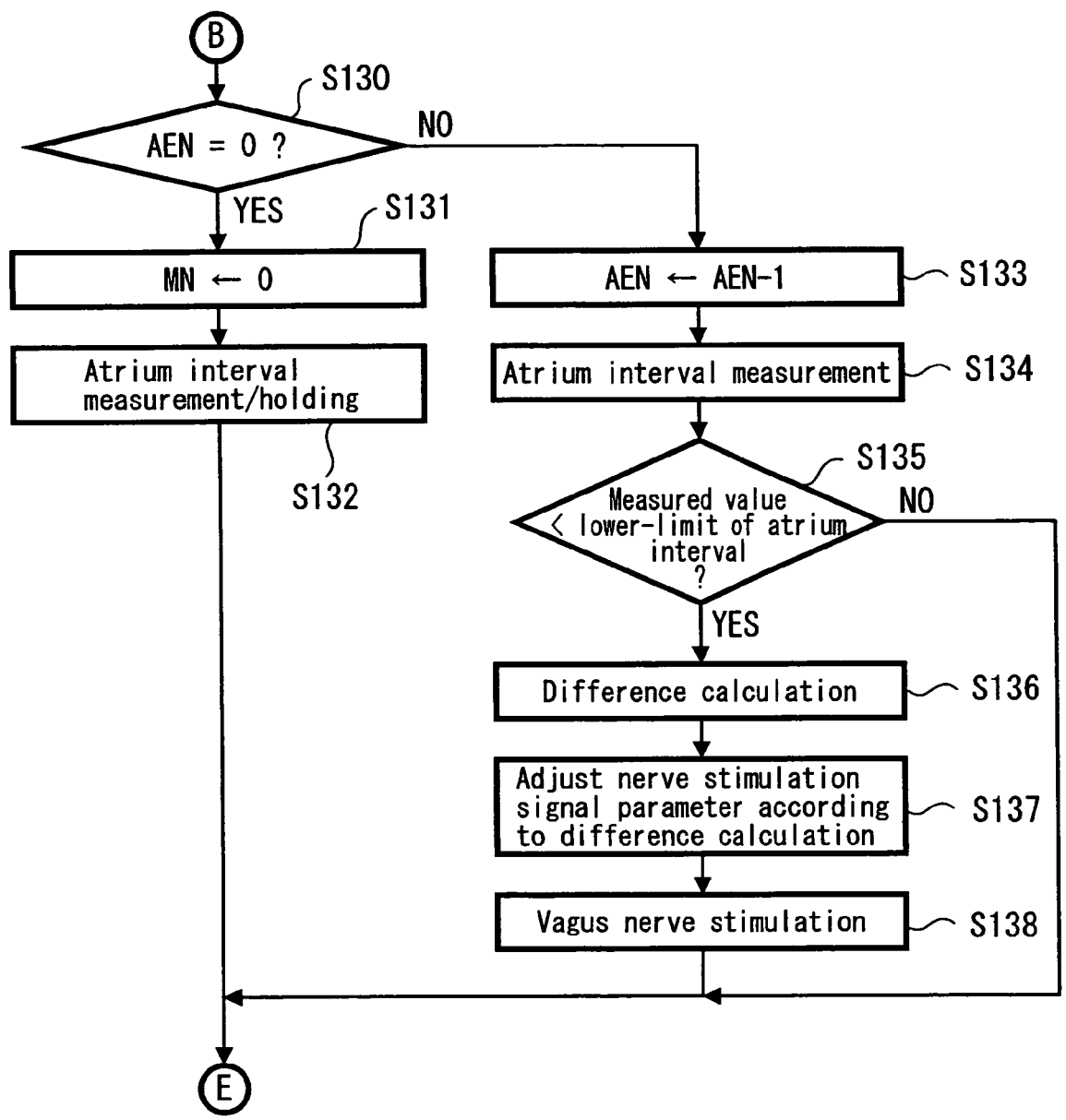
FIG. 17 is a portion of a flow diagram for explaining operation of the third exemplified embodiment according to the heart treatment apparatus of the present invention.

Next, the operation in a case when the atrium contraction was detected in judgment step S107 of FIG. 15 (after (B) of FIG. 15) will be explained according to a flow diagram of FIG. 17. When the atrium contraction is detected in judgment step S107 of FIG. 15, it is judged whether or not the atrium event number of times AEN loaded in the atrium event counter 37 is "0" (step S130). In a case when the atrium event number of times AEN=0 is true, more specifically, in a case when the nerve stimulation treatment period is ended, the maximum precursor number MN is made to be reset to "0" (step S131) and at the same time, the atrium interval measured by the atrium interval measuring unit 17 is maintained in the atrium interval holding/processing unit 40 (see FIG. 13 or FIG. 14) (step S132) and the flow returns to (E) of the flow diagram in FIG. 15.

When AEN loaded in the atrium event counter 37 is not "0" in judgment step S130, more specifically, when the nerve stimulation treatment is in an activation state, "1" is decremented from the stored atrium event number of times in the atrium event counter 37 every time on an occasion of the atrium event detection (step S133). Then, the atrium event interval detected by the atrium interval measuring unit 17 is measured (step S134).

Next, it is judged whether or not this atrium interval measured value is shorter than the lower-limit of the atrium interval calculated by the aforesaid atrium interval lower-limit calculation unit 38 (step S135). Here, when the measured value of the atrium interval measuring unit 17 is longer than or equal to the lower-limit of the atrium interval, the stimulation of the vagus nerve 35 is not carried out and the flow returns to (E) of FIG. 15. Then, when the measured value of the atrium interval measuring unit 17 is shorter than the calculated lower-limit of the atrium interval, difference between the measured value and the lower-limit of the atrium interval is calculated in the difference calculation unit 23 (step S136). The calculated difference is supplied to the nerve stimulation signal control unit 25, a nerve stimulation signal parameter is selected and degree of the nerve stimulation is adjusted (step S137). This nerve stimulation signal parameter is transmitted from the nerve stimulation signal control unit 25 to the nerve stimulation unit 6 and nerve stimulation is carried out in response to the parameter (step S138). After the nerve stimulation was carried out, the flow returns to (E) of FIG. 15.

Next, the operation flow subsequent to step S115 of FIG. 15 will be explained according to a flow diagram of FIG. 18. As shown in the flow diagram of FIG. 15, when the ventricle contraction is detected (step S114) and the clocking of the atrioventricular delay timer 18 stops, the flow proceeds to (C) of FIG. 18 and it is judged whether or not precursor was detected in the ventricle tachyarrhythmia precursor detection unit 7 (step S139). It should be noted that detection of the premature contraction is carried out in judgment step S106 of FIG. 15, so that it is judged here whether or not precursor other than premature contraction such as repolarization abnormality, ST change or the like was detected.

When precursor other than premature contraction is detected, a precursor number N corresponding to the precursor is obtained (step S140) and it is judged whether or not the precursor number N is smaller than the maximum precursor number MN (step S141). When the precursor number N is bigger than or equal to the maximum precursor number MN, the obtained precursor number N is made to be the maximum precursor number MN (step S142). Subsequently, in the atrium interval lower-limit calculation unit 38, a predetermined amount (case of FIG. 13) or a predetermined ratio (case of FIG. 14) with respect to the atrium interval measured by the atrium interval measuring unit 7 is selected according to the detected precursor number N (step S143).

Then, the lower-limit of the atrium interval is calculated in the atrium interval lower-limit calculation unit 38 according to aforesaid selected predetermined amount or predetermined ratio and the atrium interval maintained in the atrium interval holding/processing unit 40 (step S144).

Next, in the limitation unit 42 of the atrium interval lower-limit calculation unit 38, the magnitude relation between this calculated lower-limit of the atrium interval and the A-A interval stored in the A-A interval memory unit 11 is compared (step S145). When the calculated lower-limit of the atrium interval is longer than the A-A interval, the calculated lower-limit of the atrium interval is replaced by the A-A interval (step S146) and when the calculated lower-limit of the atrium interval is equal to or shorter than the A-A interval, step S146 is skipped and the calculated lower-limit of the atrium interval is made to be the lower limit of the atrium interval threshold supplied to the comparator unit 22 (step S147).

Subsequently, the atrium event number of times stored in the atrium event number table memory unit 36 is selected according to the precursor number N (step S148). Then, aforesaid selected atrium event number of times is loaded to the atrium event counter 37 (step S149) and the flow returns to (D) of FIG. 15.

As described above, there were explained about constitutions and operations of the first to the third exemplified embodiments according to the present invention, but the heart treatment apparatus of the present invention is not being obsessed with aforesaid first to third exemplified embodiment and it is needless to say that many further exemplified embodiments are included without departing from the scope of the present invention described in the claims.

According to the heart treatment apparatus of the present invention, precursor of fatal arrhythmia is detected and tolerance level of the heart rate is set depending on the severity degree of that precursor and the heart rate can be lowered and at the same time the heart rate variation can be suppressed by stimulating the vagus nerve such that the heart rate falls into the tolerance level, so that after the precursor detection, it is possible to realize reduction in oxygen consumption of the heart muscle by the heart rate lowering, non-uniformity correction of the heart muscle repolarization by the variation repression of the heart rate and further the tension repression of the antagonistic sympathetic nerve accompanying the vagus nerve stimulation, induction of the fatal arrhythmia is repressed.

DESCRIPTION OF REFERENCE NUMERALS

1 ... heart treatment apparatus
2 ... ventricle stimulation unit
3 ... ventricle contraction detection unit
4 ... atrium stimulation unit
5 ... atrium contraction detection unit
6 ... nerve stimulation unit
7 ... ventricle tachyarrhythmia precursor detection unit
8 ... atrium stimulation interval timer
9 ... interval threshold selection unit
10 ... V-A interval memory unit
11 ... A-A interval memory unit
13 ... nerve stimulation treating time table memory unit
14 ... nerve stimulation treating time timer
17 ... atrium interval measuring unit
21 ... lower-limit atrium interval table memory unit
12, 20, 22 ... comparator unit
23 ... difference calculation unit
24 ... nerve stimulation control unit
25 ... nerve stimulation signal control unit
36 ... atrium event number table memory unit
37 ... atrium event counter
38 ... lower-limit atrium interval calculation unit

The invention claimed is:

1. A heart treatment apparatus comprising:
nerve stimulation means for generating a nerve stimulation signal which stimulates a vagus nerve;
tachyarrhythmia precursor detection means for detecting a precursor of a tachyarrhythmia occurrence and generating a signal having a value corresponding to a class of the detected precursor;
heart activity measuring means for measuring a heart activity;
tolerance level defining means for defining a tolerance level of said heart activity in accordance with the signal generated by said tachyarrhythmia precursor detection means; and
control means connected to said nerve stimulation means, said tachyarrhythmia precursor detecting means, said heart activity measuring means, and said tolerance level defining means for controlling said nerve stimulation means to generate said nerve stimulation signal when an output of said heart activity measuring means is outside said defined tolerance level.

2. A heart treatment apparatus according to claim 1, wherein the precursor detection of said tachyarrhythmia occurrence is carried out according to an electrogram.

3. A heart treatment apparatus according to claim 2, wherein the precursor of said tachyarrhythmia occurrence is any one of premature contraction, ST change and repolarization abnormality.

4. A heart treatment apparatus according to claim 1, wherein said heart activity is heartbeats.

5. A heart treatment apparatus according to claim 4, wherein heartbeat measurement by said heart activity measuring means is measurement of heartbeat interval or heart rate.

6. A heart treatment apparatus according to claim 5, wherein when said measured heartbeat interval or heart rate is outside said defined tolerance level, the nerve stimulation means generates said nerve stimulation signal which includes a parameter adjusted according to difference between said measured heartbeat interval or heart rate and said defined tolerance level.

7. A heart treatment apparatus according to claim 6, wherein said parameter of said nerve stimulation signal is at least one of: i) period between pulses, ii) pulse width, iii) number of pulses, iv) pulse current, v) pulse voltage, vi) delay time, vii) rest time and viii) repetition times, or a combination of a plurality of i)-viii).

8. A heart treatment apparatus according to claim 6, wherein said control means defined said tolerance level by determining a lower limit value of said heartbeat interval or an upper limit value of said heart rate.

9. A heart treatment apparatus according to claim 8, wherein said control means defines said tolerance level based on risk of said detected precursor.

10. A heat treatment apparatus according to claim 9, wherein said control means defines said tolerance level such that when said risk is relatively high, said lower limit value of said heartbeat interval is increased or said upper limit value of said heart rate is decreased as compared with a case that said risk is relatively low.

* * * * *